US009364002B2

(12) United States Patent
Bleeker et al.

(10) Patent No.: US 9,364,002 B2
(45) Date of Patent: Jun. 14, 2016

(54) PLANT VOLATILES

(75) Inventors: Petronella Martina Bleeker, Amterdam (NL); Kai Ament, Amsterdam (NL); Paul Johan Diergaarde, Amersfoort (NL); Michiel Theodoor Jan De Both, Wageningen (NL); Robert Cornelis Schuurink, Amsterdam (NL)

(73) Assignee: Keygene N.V., Wageningen (NL)

( * ) Notice: Subject to any disclaimer, the term of this patent is extended or adjusted under 35 U.S.C. 154(b) by 1405 days.

(21) Appl. No.: 12/679,894

(22) PCT Filed: Sep. 25, 2008

(86) PCT No.: PCT/NL2008/050617
§ 371 (c)(1),
(2), (4) Date: Jul. 1, 2011

(87) PCT Pub. No.: WO2009/041814
PCT Pub. Date: Apr. 2, 2009

(65) Prior Publication Data
US 2012/0076751 A1    Mar. 29, 2012

(30) Foreign Application Priority Data

Sep. 25, 2007  (EP) ..................................... 07117153

(51) Int. Cl.
*A01N 25/00* (2006.01)
*A01N 49/00* (2006.01)
*A01N 27/00* (2006.01)
A01P 17/00 (2006.01)

(52) U.S. Cl.
CPC ................ *A01N 49/00* (2013.01); *A01N 27/00* (2013.01)

(58) Field of Classification Search
CPC .... A01N 65/00; A01N 2300/00; A01N 25/02
See application file for complete search history.

(56) References Cited

U.S. PATENT DOCUMENTS

| 4,219,570 | A  | * | 8/1980 | Inazuka et al. ................. 514/731 |
| 2003/0194454 | A1 | * | 10/2003 | Bessette et al. ............... 424/745 |
| 2004/0077713 | A1 | * | 4/2004 | Maupin .................. A01N 27/00 514/475 |
| 2005/0008714 | A1 | * | 1/2005 | Enan .............................. 424/745 |
| 2007/0004686 | A1 | * | 1/2007 | Bengtsson et al. ............ 514/159 |

FOREIGN PATENT DOCUMENTS

| EP | 0 583 774 B1 | 2/1994 |
| JP | 11-279583 A | 10/1999 |
| RU | 2218762 C1 | 12/2003 |
| WO | WO 00/21364 A2 | 4/2000 |
| WO | WO 01/67868 A2 | 9/2001 |
| WO | WO 2005/046330 A1 | 5/2005 |
| WO | WO 2006/077568 A1 | 7/2006 |

OTHER PUBLICATIONS

Bellows, "Biological control sought for ash whitefly", California Agriculture 44(1):4-6, 1990).*
International Search Report corresponding to PCT/NL2008/050617, dated Dec. 12, 2008, 5 pages.
J. A. Freitas et al.: "Inheritance of foliar zingiberene contents and their relationship .to trichome densities and whitefly resistance in tomatoes" Euphytica, Kluwer Academic Publishers, DO, vol. 127, Jan. 1, 2002, pp. 275-287, XP002465422.
G. F. Antonious et al.: "Zingiberene and Curcumene in Wild Tomato" Journal of Environmental Sciences and Health B: Pesticides, vol. 38, Jan. 1, 2003, pp. 489-500, XP009094369.
Zhang et al.: "Repellency of Ginger Oil to Bemisia Argentifolii (Homoptera: Aleyrodidae) on Tomato" Journal of Economic Entomology, Entomological Society of America, Landham, MD, US, vol. 1. 97, No. 4, Jan. 1, 2004, pp. 1310-1318, XP001538004.
A. F. Traboulsi et al.: "Repellency and toxicity of aromatic plant extracts against the mosquito *Culex pipiens molestus* (Diptera: Culicidae)" Pest Management Science, Wiley &Sons, Bognor Regis, GB, vol. 61, Jan. 20, 2005, pp. 597-604, XP002465423.
B.S. Park et al.: "Monoterpenes From Thyme (*Thymus vulgaris*) as Potential Mosquito Repellents" Journal of the American Mosquito Control Association, The Association, Fresno, CA, US, vol. 21, No. 1,2005, pp. 80-83, XP009075264.
M. O. Omolo et al.: "Repellency of essential oils of some Kenyan plants against Anopheles gambiae" Phytochemistry, Pergamon Press, GB, vol. 65, Jan. 1, 2004, pp. 2797-2802, XP004609876.
A. Tawatsin et al.: "Repellency of essential oils extracted from plants ,in Thailand against four mosquito vectors (Diptera: Culicidae) and oviposition deterrent effects against Aedes aegypti (Diptera: Culicidae)" Southeast Asian Journal of Tropical Medicine and Public Health, Project Od Seameo, Bangkok, vol. 37, No. 5,2006, pp. 915-931, XP009094383.
M. Pareja et al.: "Response of the Aphid Parasitoid Aphidius funebris to Volatiles from Undamaged and Aphid-infested,Centaurea nigra" Journal of Chemical Ecology, Kluwer Academic Publishers—Plenum Publishers, NE, vol. 33, No. 4. Mar. 2, 2007, pp. 695-710, XP019481456.
G. Antonious et al.: "Natural Products: Repellency and Toxicity of Wild Tomato Leaf Extracts to the Two-Spotted Spider Mite, *Tetranychus urticae* Koch" Journal of Environmental Sciences and Health B: Pesticides, vol. 41, No. 1, Jan. 1, 2006, pp. 43-55, XP009094386.
T.G.T. Jaenson et al.: "Evaluation of extracts and oils of mosquito (diptera: culicidae) repellent plants from Sweden and Guinea-Bissau" Journal of Medical Entomology, Entomological Society of America, Lanham, MD, US, vol. 43, No. 1, Jan. 1, 2006, pp. 113-119, XP009094387.
A.E. Stuart et al.: "A microscope slide test for the evaluation of insect repellents as used with Culicoides impunctatus" Entomologia Experimentalis Et Applicata, Kluwer Academic Publishers, Dordrecht, NL, '101.89, Jan. 1, 1998, pp. 277-280, XP002465425.
Antonious, "Production and Quantification of Methyl Ketones in Wild Tomato Accessions", Journal of Environmental Science and Health, Part B: Pesticides, Food Contaminants, and Agricultural Wastes, 2001, vol. 36, No. 6, pp. 835-848.

(Continued)

*Primary Examiner* — Robert T Crow
*Assistant Examiner* — John P Nguyen
(74) *Attorney, Agent, or Firm* — Foley & Lardner LLP; Sunit Talapatra

(57) ABSTRACT

The present invention provides compounds and compositions for attracting or repelling sap-sucking insects, such as whitefly, as well as methods for using such compositions.

22 Claims, 7 Drawing Sheets

(56) References Cited

OTHER PUBLICATIONS

Figure 1A:
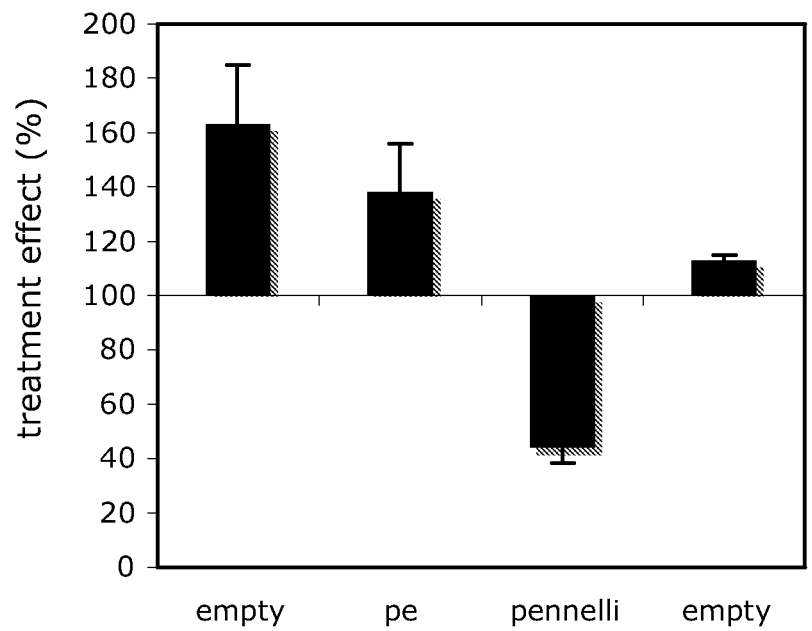

Antonious, et al. "Natural Products: Seasonal Variation in Trichome Counts and Contents in Lycopersicum hirsutum f. glabratum", Journal of Environmental Science and Health, Part B: Pesticides, Food Contaminants, and Agricultureal Wastes, 2005, vol. 40, pp. 619-631.
Bruce, et al., "Insect host location: a volatile situation", Trends in Plant Science, Jun. 2005, vol. 10, No. 6, pp. 269-274.
Kauffman, et al. "Inhibition of Campoletis sonorensis Parasitism of Heliothis zea and of Parasitoid Development by 2-Tridecanone-Mediated Insect Resistance of Wild Tomato", Journal of Chemical Ecology, 1989, vol. 15, No. 6, pp. 1919-1930.
Kostyukovsky, et al., "The Potential use of Plant Volatiles for the Control of Stored Product Insects and Quarantine Pests in Cut Flowers", Acta Horticulturae, 2002, vol. 576, pp. 347-358.
The Examination Report received in the related Australian Patent Application No. 2008304003, dated Feb. 5, 2013.
Awords, G. et al., "Composition of Australian Tea Tree Oil (*Melaleuca alternifolia*)", *Journal of Agricultural Food Chemistry*, 1978, vol. 26, No. 3, pp. 734-737.
Breedon, D.C., et al., "7-Epizingiberene, a Novel Bisabolane Sesquiterpene From Wild Tomato Leaves", *Tetrahedron*, 1994, vol. 50, issue 38, pp. 11123-11132.
Carson, et al., "*Melaleuca alternifolia* (Tea Tree) Oil: a Review of Antimicrobial and Other Medicinal Properties", *Clinical Microbiology Reviews*, 2006, vol. 19, No. 1, pp. 50-62.
Freitas, J.A. et al., "Inheritance of Foliar Zingiberene Contents and Their Relationship to Trichome Densities and Whitefly Resistance in Tomatoes", *Euphytica*, 2002, vol. 127, pp. 275-287.
Gorski, R., "Effectiveness of Natural Essential Oils in the Monitoring of Greenhouse Whitefly (*Trialeurodes vaporariorum* Westwood)", *Folia Horticulturae*, 2004, Annals 16-1, pp. 183-187.
Shawl, A.S. et al., "Cultivation of Rose Scented Geranium (*Pelargonium* sp.) as a Cash Crop in Kashmir Valley", *Asian Journal of Plant Sciences*, 2006, vol. 5, issue 4, pp. 673-675.
Smith, R.M. et al., "Comparison of Volatiles and Waxes in Leaves of Genetically Engineered Tomatoes", *Phytochemistry*, 1996, vol. 43, No. 4, pp. 753-758.
Wilson, C.W. II, et al, "Quantitative Composition of Cold-Pressed Grapefruit Oil", *Journal of Agricultural and Food Chemistry*, 1978, vol. 26, No. 6, pp. 1432-1434.

\* cited by examiner

PLANT VOLATILES

CROSS-REFERENCE TO RELATED APPLICATIONS

This is a National Stage application of PCT/NL2008/050617, filed Sep. 25, 2008, which claims the benefit and priority of European Patent Application No. 07117153.2, filed Sep. 25, 2007. The foregoing applications are incorporated by reference herein in their entirety.

FIELD OF THE INVENTION

The present invention relates to the field of agriculture, in particular insect pest control of plants. Compounds and compositions comprising one or more volatile hydrocarbon compounds suitable for either repelling or attracting insect pests, such as whiteflies, are provided. Also provided are methods for making and using attractant or repellent compounds/compositions and for controlling insect infestation and damage in the field and/or in greenhouses. The compositions are suitable for controlling plant insect pests, in particular sap-sucking insects of the suborder Sternorrhyncha. Insects of the suborder Sternorrhyncha include psyllids, whiteflies, aphids, mealybugs and scale insects and share a common property, namely the utilization of plant sap as their food source. Other plant insect pests which can be controlled are thrips, mites (e.g. spider mites) and leaf hoppers. In a preferred embodiment methods and compositions for controlling whitefly infestation and whitefly damage of crop plants are provided. In a different embodiment, the compounds and/or compositions can be used for repelling insects of the family Culicidae, especially species belonging to the genera *Anopheles* (of which about 400 species exist, 30-40 of which transmit malaria, such as the species of the *A. gambiae* complex), *Culex* and/or *Aedes*. Also members of the family Ceratopogonidae, biting midges, can be attracted or repelled according to the invention, for examples the vertebrate blood sucking genera *Culicoides, Forcipomyia* (*Lasiohelea*), and *Leptoconops*, such as *Culicoides impunctatus* (the highland midge or Scottish biting midge).

BACKGROUND OF THE INVENTION

Whiteflies of the genera *Bemisia* (sweet potato whitefly) and *Trialeurodes* (greenhouse whitefly) are major pests of crop plants throughout the world, causing economic losses especially due to the transmission of plant viruses during feeding (i.e. they act as 'virus vectors'). *Bemisia tabaci* is capable of transmitting more than 60 different Geminiviridae plus a number of criniviruses, many of which belong to the Begomoviruses such as African cassava mosaic virus (ACMV), Bean golden mosaic virus (BGMV), Bean dwarf virus, Tomato yellow leaf curl virus (TYLCV), Tomato mottle virus (TMV), and others. Both tropical and temperate crops are affected, such as tomatoes, beans, cucurbits, potatoes, cotton, cassava and sweet potatoes. To date, the main control strategy is the application of insecticides, aimed at killing adults, juveniles and eggs. Besides the substantial costs of insecticide application this practice has a severe environmental impact. Moreover, *B. tabaci* is difficult to control with insecticides due to emerging resistance to the active ingredients.

In order to reduce insecticide application, there is a need for new ways of controlling whitefly-induced crop damage and losses, both in field-grown and greenhouse-grown crops. From literature it is known that volatile components can directly influence insect behaviour (e.g. Bruce et al., 2005, Trends Plant Sci. 10: 269-74). One way to control virus transmission by whiteflies is by identifying insect repellents, which can be applied on or near the crop plants, and/or insect attractants, which can be applied on nearby areas to lure the insect pests away from the crop. The problem in identifying attractants and/or repellents is that compounds that are known to attract one species may repel another species of insects. Often one cannot, therefore, draw conclusions about the attractant or repellent properties of compounds or compositions across species which may differ in their sensory perception and feeding behavior. Whiteflies, for example, investigate their host plants by labial dabbing (using mechanosensors and chemo sensors) on the epidermal surface, before tapping into the vascular tissue (probing). Their decision at this point is influenced by e.g. constitutively produced repellents but probably also by properties of the leaf surface. Preference is directly related to performance and virus transmission, which occurs upon probing. In order to avoid virus transmission, probing should be prevented or at least reduced significantly. This means compounds that kill the whiteflies only after probing has occurred are not suitable as crop protection agents, as the virus will already have been transferred. In addition, insect predators of whiteflies should not be affected by the repellent or attractant, as these are useful in reducing the whitefly population.

Another problem in identifying suitable compounds and/or compositions for whitefly control lies in the fact that naturally occurring plant headspace compositions and the content of the glandular trichomes of plants contain a large number of different compounds in different concentrations, which vary between species and between individual plant lines or accessions within species. Even if a plant headspace composition as a whole is identified in having a certain effect on insect pests, identifying which components, or combinations of components, may be suitable as attractants or repellents is no easy task and to date there is no suitable repellent or attractant for whiteflies and other sap-sucking insect pests.

Zhang et al. (J. Econo Entomolog 2004, 97, p 1310-1318) tested 0.25% solutions of ginger oil as a repellent for *B. argentifolii*. In no-choice tests, only between 10.2 and 16.6% fewer adult whiteflies settled on the treated plants and no difference was found in the numbers of eggs laid on the plants. Increasing the concentration of ginger oil was associated with phytotoxicity, thereby preventing an effective use of ginger oil as whitefly repellent.

EP 0 583 774 describes the use of vegetable oil to reduce phytotoxicity of foliar insect control agents, whereby any type of insect control agent may be used.

Glandular trichomes are prominent on foliage and stems of the genus *Lycopersicon* (now classified as *Solanum*) and have been shown to produce a large number of secondary compounds, such as sesquiterpene hydrocarbons, sesquiterpene acids, methylketones and sugar esters. Several studies have tried to correlate the density of glandular trichomes with resistance against plant pests, such as maize earworm (*Heliothis zea*) or Colorado beetle (Kauffman and Kennedy, 1989, J Chem Ecol 15, 1919-1930; Antonious, 2001, J Environ Sci Health B 36, 835-848 and Antonious et al. 2005, J Environ Sci Health B 40: 619-631). Also the methylketones 2-undecanone and 2-tridecanone, stored in the glandular trichomes of *L. hirsutum f. glabratum* were shown to exhibit a toxic effect against fourth instar larvae of Colorado potato beetle and adult whiteflies *B. tabaci*, respectively (Antonious et al. 2005, J Environ Sci Health B 40: 619-631).

Antonious and Kochhar (J Environm Science and Health B, 2003, B38: 489-500) extracted and quantified zingiberene and curcumene from wild tomato accessions with the goal of selecting wild tomato accessions that can be used for the production of sesquiterpene hydrocarbons for natural insecticide production. However, whether such compounds are able to be used as whitefly repellents or attractants was not disclosed. It is mentioned that zingiberene has been associated with Colorado beetle resistance and beet armyworm resistance, while curcumene has been associated with insecticidal effects. The wild tomato species *L. hirsutum f. typicum* is mentioned to be resistant to *B. argentifolii* (Heinz et al. 1995, 88:1494-1502), but trichome based plant resistance could, of course, have various causes and from this paper one cannot make inferences regarding the presence or identity of compounds which have properties for attracting or repelling whiteflies.

Kostyukovsky et al. (Acta Horticulturae 2002, 576, 347-358) found that fumigants of essential plant oils (Cineole, safrole, essential oil from Labiatae or *Foeniculum vulgare*, or M-bromide) applied on pests of cut flowers (e.g. *B. tabaci*) at concentrations of 10-20 mg/l caused mortality after 2-4 hours of exposure (see Table 5).

Freitas et al. (Euphytica 2002, 127: 275-287) studied the genetic inheritance of the genes for the production of both the sesquiterpene zingiberene and glandular trichome types I, IV, VI and VII in interspecific crosses between *L. esculentum* (cultivated tomato, low in zingiberene) and wild *L. hirsutum* var. *hirsutum* (high in zingiberene). Zingiberene content in $F_2$ plants contributed to *B. argentifolii* resistance by correlation and it was suggested to breed plants with simultaneously high levels of zingiberene, 2-tridecanone and/or acylsugars to contribute to higher levels of whitefly resistance. However, breeding for pest resistance is fundamentally different from developing pest repellent or attractant compositions. There is no indication as to the use of synthetic or purified zingiberene as whitefly repellent as such or in combination with other compounds.

SUMMARY OF THE INVENTION

The present inventors found 10 terpenes (or terpene analogues) to be related to repellance/attractance of sap-sucking insect pests, in particular whiteflies. These compounds can be used individually or in combination to make effective insect repellent and/or insect attractant compositions. Provided are insect repellent compositions (in particular repelling sap-sucking insect pests of crop plants, preferably whitefly) comprising or consisting of one or more of the following seven compounds: curcumene, especially alpha-curcumene (sesquiterpene), myrcene, especially beta-myrcene (monoterpene), cymene, especially para-cymene (hydrocarbon related to monoterpene), terpinene, especially gamma-terpinene (monoterpene) and/or alpha-terpinene (monoterpene), zingiberene (sesquiterpene) and/or phellandrene, especially alpha-phellandrene (monoterpene) as well as methods of using these and dispensers or other containers or supporting material comprising these.

Provided are insect attractant compositions (in particular attracting sap-sucking insect pests of crop plants, preferably whitefly) comprising or consisting of one or more of the following three compounds: Phellandrene, especially beta-phellandrene (monoterpene), limonene (the D- and/or L-isomer) (monoterpene) and/or 2-carene (monoterpene), as well as methods of using these and dispensers or other containers or material comprising these.

In a further embodiment of the invention the above repellent or attractant compounds or compositions are used to attract or repel insects of the family Culicidae (order Diptera) and/or Ceratopogonidae, especially blood sucking insects that are irritant and potentially transmit diseases to humans and animals, such as mosquitoes.

GENERAL DEFINITIONS

"Plant insect pests" or "plant pests" or "insect pests" or "plant pest species" are insect species that cause infestation and damage on crop and/or ornamental plants (hosts plant species), by infestation of the plants or plant parts. An "infestation" is the presence of a large number of pest organisms in an area (e.g. a field or glasshouse), on the surface of a host plant or on anything that might contact a host plant, or in the soil. Insect pests include sap-sucking insect pests (see below), but also other insect pests, such as thrips, cicada, mites (e.g. spider mites and others) and leaf-hoppers.

"Mammalian insect pests" or "mammalian disease vectors" refer herein to insects of the order Diptera which are blood-sucking/biting insects and are potentially able to act as vectors of human and/or mammalian diseases (but not necessarily, they may just be irritating), such as malaria. When referring to "insect pests" herein, it is understood that the parts of the document also apply to insects attacking animals, especially mammals, in an analogous way to plant pests, except that these are blood sucking/biting insects.

"Sap-sucking insect pests" include plant pests of the suborder Sternorrhyncha (of the order Hemiptera, of the class Insecta), i.e. insect pests which include psyllids, whiteflies, aphids, mealybugs and scale insects and share a common property, namely the utilization of plant sap as their food source.

"Aphids" include herein plant insect pests of the family Aphididae, such as *Aphis gossypii, A. fabae, A. glycines, A. nerii, A. nasturtii, Myzus persicae, M. cerasi, M. ornatus, Nasonovia* (e.g. *N. ribisnigri*), *Macrosiphum, Brevicoryne* and others.

"Insect vectors" are insects that are capable of carrying and transmitting viruses to plants. In the context of mammalian disease vectors, insect vectors are insects which attack mammals and can potentially transmit diseases to mammals, such as mosquitoes, which are able to transmit the parasite *Plasmodium* to humans or heartworm to canines.

"Whitefly" or "whiteflies" refer to species of the genus *Bemisia*, especially *B. tabaci* and *B. argentifolii* (also known as biotype B of *B. tabaci*), and/or species of the genus *Trialeurodes*, especially *T. vaporariorum* (greenhouse whitefly) and *T. abutinolea* (banded winged whitefly). Included herein are all biotypes, such as biotype Q and B of *B. tabaci*, as well as any developmental stage, such as eggs, larvae, pupae and adults.

"Repellent" compound or composition refers to one or more compounds, which repel one or more insect pest species (e.g. whiteflies), and significantly reduce the infestation and/or damage caused by the insect pest (e.g. whiteflies) in the area and/or surfaces applied, compared to the same area and/or surfaces not treated with the repellent (measured at one or more time points after repellent application). A "significant reduction" is a reduction by at least 5 number %, preferably at least 10%, 15%, 20%, 30%, 50%, 60%, 70%, 80%, 90%, 95% or more (100%). Infestation and/or damage caused by the insect pests(s) (e.g. by whitefly) can be measured in various ways, e.g. by assessing the plant health or by assessing e.g.

insect pest numbers, insect eggs laid, insect probing of the tissue, virus transmission or incidence, yield losses, plant tissue damage, or any other direct or indirect symptoms of insect infestation/damage, etc. In the context of mammalian insect pests, for example the number of insects, insect bites or disease symptoms can be used to assess and/or quantify the effect.

"Attractant" compound or composition refers to one or more compounds, which attract one or more insect pest species (especially sap-sucking insect pests, such as whiteflies) and significantly increase the number of the pest organisms (e.g. whiteflies) in the area and/or surfaces applied, compared to the same area and/or surfaces without the attractant (measured at one or more time points after attractant application). A "significant increase" is an increase by at least 5 number %, preferably at least 10%, 15%, 20%, 30%, 50% 60%, 70%, 80%, 90%, 95%, or more. When the attractant is applied to plant tissues, the attractant effect can be measured in various ways, for example by assessing the number of insects at one or more time-points after application of the attractant, or by assessing tissue damage or other symptoms associated with insect infestation/damage. When the attractant is applied to other supporting materials, such as non-biological materials/areas (traps, solid supports, etc.), the numbers of insects on the treated versus the non-treated material/areas is assessed. In the context of mammalian insect pests, for example the number of insects can be used to assess and/or quantify the effect (attraction).

An "effective amount" of a repellent compound or composition refers to an amount sufficient to significantly decrease the infestation and/or damage caused by insect pests (especially by one or more sap-sucking insect pests such as whiteflies) on treated plants compared to untreated plants. In the context of mammalian insect pests, an effective amount of a repellent compound or composition refers to an amount sufficient to significantly repel the insects as defined above.

An "effective amount" of an attractant compound or composition refers to an amount sufficient to significantly increases the number of insect pests (especially by one or more sap-sucking insect pests such as whiteflies and/or stages thereof, e.g. eggs laid) in the treated area or on the treated surfaces compared to the untreated area or surfaces. In the context of mammalian insect pests, an effective amount of a repellent compound or composition refers to an amount sufficient to significantly attract the insects as defined above.

"Active ingredient" refers to the ingredient/s in a formulation which is/are biologically active, e.g. insect vector/pest repellents or attractants. "Inert ingredient" or "inactive" refers to ingredients which are not biologically active (at least regarding the target insect vectors), such as carriers of the active ingredient(s), e.g. water, oil or oil-based carriers, solvents, etc.

"Solvent" is a liquid that dissolves a solid, liquid, or gaseous solute, resulting in a solution, dispersion or emulsion.

"Traps" refer to materials to which an effective amount of an attractant compound or composition is applied. Generally a trap may be a plurality of plants (trap-crop or trap plants) or a container (e.g. an insect trap) or surface or liquid to which the attractant compound or composition is applied, so that the insects are lured towards or into/onto the trap. The attractant compound or compositions may also be referred to as "bait formulation".

"Insecticides" or "insecticidal" refers to compounds or compositions that (in contrast to repellents) kill or inactivate one or more stages of an insect (ovicides, larvicides, adulticides, etc.), i.e. they affect mortality rather than distribution of the insects.

'Insect-pest predators or "insect-pest parasites" refer herein to organisms that feed on or parasitize the insect pest. For example "whitefly predators" or "parasites" refer herein to organisms, such as insect species, which reduce whitefly numbers by predation and/or parasitism, such as broad mite (*Polyphagotarsonemus latus*), Swirski-mite (*Amblyseius swirskii*), lacewings, various beetles, etc., or parasitic wasps (such as Encarsia and *Eretmocerus* spp.).

"Host plant(s)" refer to one or more species which are natural host species of insect pests. Whitefly, for example, has a broad host range, such as, but not limited to, tomato, pepper, eggplant, lettuce, *Brassica* species, such as oilseed rape, broccoli, cauliflower and cabbage crops; cucurbits such as cucumber, melon, pumpkin, squash; peanut, soybeans, cotton, beans, cassava, potatoes, sweet potatoes and okra. Also ornamental species are among the preferred hosts, such as hibiscus, poinsettia, lilies, iris, lantana rose and petunia.

"Crop" or "crop plants" or "cultivated plants" refer to plants which are grown by humans for various purposes, such as but not limited to obtaining food-, feed- or any other ingredient from the plants or plant parts, including plant-derived products such as oil, carbohydrates, medicinal ingredients, etc., but also including plants cultivated for ornamental purposes or for socio-economic purposes, such as lawns (grass-grown areas) of e.g. golf courses, playgrounds or parks, or plants grown in forests or parks, etc. Crop plants may be grown in the field, in gardens, in greenhouses or any other way, and they may be grown on a small or on a large scale.

Recently tomato has been reclassified into the *Solanum* genus. Throughout this document "*Lycopersicon esculentum*" and "*Solanum lycopersicum*" are used interchangeably to refer to cultivated tomato plants. Similarly, when referring to wild tomato the *Lycopersicon pennelli* and *Solanum pennelli*, as well as *Lycopersicon hirsutum f. glabratum* and *Lycopersicon hirsutum f. typicum* and *Solanum habrochaites*, are used interchangeably. Similarly, when referring to wild *Lycopersicon* species, it is understood that these are now re-classified as belonging to the genus *Solanum* and these genera designations are used interchangeably.

"Terpenes" are hydrocarbons having a carbon skeleton derived from isoprene units and are subdivided into groups based on their carbon number, e.g. C10 monoterpenes, C15 sesquiterpenes, C20 diterpenes, C25 sesterterpenes, C30 triterpenes, C40 tetraterpenes and C5n polyterpenes. They are herein generally referred to by their trivial names, as e.g. described in Kirk-Othmer, Encyclopedia of Chemical Technology, 4$^{th}$ Ed., Vol. 23, pages 833-882, 1997. The term "terpene(s)" as used herein also includes compounds commonly known as "terpenoids", terpene and/or terpenoid analogues, such as alcohols, esters, aldehydes and ketones, (natural or synthetic) isomers, and where applicable stereoisomers and/or tautomers of any of these. When referring to specific isomers herein (such as alpha and/or beta isomers), it is understood that other isomers are included and that the other isomers or mixtures of isomers can substitute for the isomer specifically mentioned, as long as these are functional.

Monoterpenes may further be distinguished by the structure of the carbon skeleton and may be grouped into "acyclic monoterpenes" (e.g. myrcene, (Z)- and (E)-ocimene, linalool, geraniol, nerol, citronellol, myrcenol, geranial, citral a, neral, citral b, citronellal, etc.), "monocyclic monoterpenes" (e.g. limonene, alpha- and gamma-terpinene, alpha- and beta-phellandrene, terpinolene, menthol, carveol, etc.), "bicyclic monoterpenes" (e.g. alpha-pinene, beta-pinene, myrtenol, myrtenal, verbanol, verbanon, pinocarveol, etc.) and "tricyclic monoterpenes" (e.g. tricyclene). See Kirk-Othmer, Encyclopedia of Chemical Technology, 4$^{th}$ Ed., Vol. 23, pages 834-835, 1997.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

Whenever reference to a "plant" or "plants" (or a plurality of plants) is understood to also refer to plant parts (cells, tissues or organs, seeds, severed or harvested parts, leaves, seedlings, flowers, pollen, fruit, stems, roots, callus, protoplasts, etc), progeny or clonal propagations of the plants which retain the distinguishing characteristics of the parents, such as seed obtained by selfing or crossing, e.g. hybrid seed (obtained by crossing two inbred parental lines), hybrid plants and plant parts derived therefrom are encompassed herein, unless otherwise indicated.

DETAILED DESCRIPTION

The invention relates in one embodiment to compounds, and compositions comprising or consisting of one or more of these, which have insect repellent or insect attractant properties.

Compounds and Compositions

Whiteflies make use of both visual cues and chemical cues to find their host plant. In free choice recapture-assays with tomato plants, wherein visual cues were removed, it was found whiteflies had a preference for the cultivated *L. esculentum* (cultivar Moneymaker) over various wild tomato species (*Solanum pennelli*, LA716; *Solanum habrochaites f. typicum*, PI27826; *Solanum habrochaites f. glabratum*, also referred to as *L. hirsutum f. glabratum*; PI126449). When the headspace of wild tomato plants was removed, dissolved in pentane-ether and added (on a filter-paper carrier) to the cultivated Moneymaker, this cultivar became up to 60% less attractive to whiteflies (*B. tabaci*, biotype Q), while the application of the control (the solvent pentane-ether) had no effect on attraction/repellency. See Example 1.

In a large experiment (see Example 2), the headspace of 16 wild tomato accessions and 5 cultivated tomato lines were sampled and analyzed (6 repeats). In total 51 compounds were identified to be present in the captured headspace. Furthermore, the level of repellency/attraction of each of the 21 tomato accessions was established in free choice bioassays with *B. tabaci* (biotype Q), using a ranking scale of 1-7 (1=highest repellency to 7=lowest repellency). Next, the identified volatile compounds were correlated to the repellency/attraction score of each tomato accession through a linear regression analysis. Eventually 7 volatile components were found to be related to whitefly repellence and 3 volatile components were shown to be correlated to whitefly attraction (Table 1).

TABLE 1

| Volatile aromatic hydrocarbons | | |
|---|---|---|
| Volatile compound (common name) | Effect on insects | Chemical structure, chemical name, (CAS Registry number) |
| alpha-curcumene | Repellent | 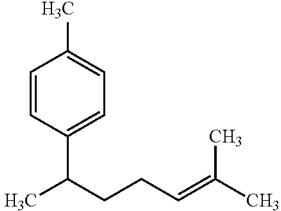<br>1-(1,5-Dimethyl-4-hexenyl)-4-methylbenzene (644-30-4) |
| beta-myrcene | Repellent | 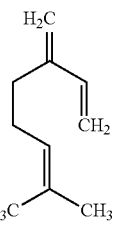<br>1,6-Octadiene, 7-methyl-3-methylene (123-35-3) |
| para-cymene | Repellent | 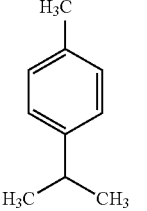<br>benzene, 1-methyl-4-(1-methylethyl) (99-87-6) |
| gamma-terpinene | Repellent | 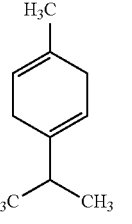<br>1,4-cyclohexadiene, 1-methyl-4-(1-methylethyl)-(99-85-4) |
| zingiberene | Repellent | 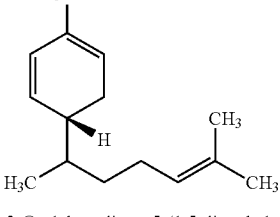<br>1,3-Cyclohexadiene, 5-(1,5-dimethyl-4-hexenyl)-2-methyl-(495-60-3) |

TABLE 1-continued

Volatile aromatic hydrocarbons

| Volatile compound (common name) | Effect on insects | Chemical structure, chemical name, (CAS Registry number) |
|---|---|---|
| Alpha-terpinene | Repellent | 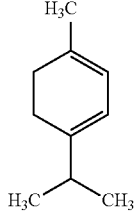 |
| Alpha-phellandrene | Repellent | 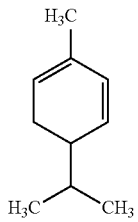 |
| beta-phellandrene | Attractant | 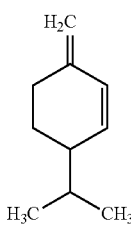<br>methyl-6-(1-methylethyl) cyclohexene <3-> (555-10-2) |
| limonene | Attractant | 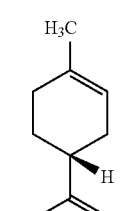<br>methyl-4-(1-methylethenyl) cyclohexene <1-> (138-86-3) |
| 2-carene | Attractant | 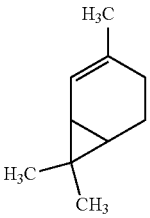<br>bicyclo [4.1.0] hept-2-ene, 3,7,7-trimethyl- (554-61-0) |

The whitefly repellent or attractant properties of the individual, pure compounds described in Table 1 (chemically synthesized or bought from commercial suppliers) were confirmed in bioassays (Example 3). Further, mixtures of two or more repellents or two or more attractants are tested for efficacy and possible synergistic effects. A direct link between *B. tabaci* response and the (individual or mixtures of) compounds of Table 1 is confirmed in antennae-electrophysiological experiments using an adapted Olfactory Detector Port (Example 4). In this way the individual volatile compounds of Table 1, or mixtures of two or more compounds of Table 1, are put into direct contact with the antennae of the whitefly through electrodes and a EAD-potential (Electroantennographic detection) is established.

The above findings can be extended to other insect pests, such as other sap-sucking insects, thrips, mites and others, such as mammalian insect pests. Thrips include for example *Thrips tabaci, Frankliniella occidentalis, Thrips fuscipennis, Echinothrips americanus* and others. Mites include for example the so called spider mites (family Tetranychidae), thread-footed mites (family Tarsonemidae), and the gall mites.

Thus, in one embodiment the present invention provides an insect repellent (especially a sap-sucking insect repellent, a thrips and/or a mite repellent, preferably at least a whitefly repellent) composition comprising or consisting of an effective amount of one or more of: alpha-curcumene, beta-myrcene, para-cymene, gamma-terpinene, alpha-terpinene, alpha-phellandrene and/or zingiberene.

Combinations of two or more repellent compounds include the following preferred combinations:
  epizingiberene in combination with S-curcumene;
  beta-myrcene in combination with para-cymene and/or gamma or alpha terpinene, S-curcumene and/or zingiberene;
  para-cymene and beta-myrcene and/or gamma-terpinene;
  para-cymene and alpha-terpinene and/or alpha-phellandrene;
  any combination of 2, 3, 4, 5, 6 or 7 of the repellent compounds, whereby the combination preferably does not occur in nature and/or does not occur in the purity (absence of other compounds), concentration and/or ratios provided herein;

In another embodiment the present invention provides an insect attractant (especially a sap-sucking insect attractant, thrip and/or mite attractant, preferably at least a whitefly attractant composition comprising or consisting of an effective amount of one or more of: beta-phellandrene, limonene and/or 2-carene. Combinations of two or more attractant compounds include therefore the following combinations:
  beta-phellandrene and limonene;
  beta-phellandrene and 2-carene;
  limonene and 2-carene; and
  beta-phellandrene limonene and 2-carene.

For one or more different insect pests the ranking of the above compounds with respect to their attraction or repellence effect may vary. Which of the 7 repellent compounds is individually most effective as repellent of one or more insect pests, and which of the 3 attractant compounds is individually most effective as attractant of one or more insect pests (preferably sap-sucking insects pests, thrips and/or mites; most preferably at least whitefly), can be tested in bioassays as described elsewhere herein or as adapted therefrom.

Similarly, which combinations of two or more compounds selected from either the 7 repellents or from the 3 attractants are most effective with respect of attracting or repelling one or more insect pests can be tested without undue experimentation using a bioassay, as described elsewhere herein. A synergistic combination is a combination where the effect of applying the compounds together (e.g. as a mixture or consecutively to the same area) is larger than the effect achieved when applying the compounds individually.

When mixtures of two compounds are used, various ratios may be most effective in attracting or repelling one or more insect pests. Ratios which may be suitable are 100:1, 50:1, 10:1, 5:1, 2:1, 1:1, 1:2, 1:5, 1:10, 1:50, 1:100 or any ratio in between.

When mixtures of three compounds are used, suitable ratios may include 1:1:1, 1:2:1, 1:2:2, 1:10:10, etc. See also Table 3 for suitable ratios. The skilled person will be able to determine which ratio is the most suitable for a particular insect species.

In one embodiment of the invention the composition comprising or consisting of (an effective amount of) at least one, two, three or more of the attractant or repellent compounds selected from the above group is substantially (i.e. >90%, especially >95%, >98% or >99%) or completely (i.e. 100%) free of other, not selected terpene or terpenoid compounds, especially non-selected terpene and/or terpenoid compounds produced naturally by plants. The compositions thus comprises as active ingredient(s) only effective amounts of the selected compounds or combination of compounds. The compositions are, therefore not natural headspace compositions of plants (i.e. as occurring in nature as headspace of non-transgenic plants, such as cultivated or wild plants), as these natural headspace compositions contain a large variety of terpenes and terpenoids. These natural headspace compositions may vary over time and under different environmental conditions. In contrast, the compositions according to the invention are defined compositions.

The compounds may be made by chemical synthesis (Millar et al., 1998, J. Nat. Prod 61:1025-1026) or may be purified from natural sources, such as plants, plant tissue(s) or headspaces, using methods known in the art, such as distillation (Agarwal et al., 2001, Pest Man. Sci., 57:289-300), in vivo production (Colby et al., 1998, PNAS 95: 2216-2221; Chang et al., 2007, Nat. Chem. Biol., 3: 274-277) and/or conventional solvent extraction, as e.g. commonly used for obtaining components of essential/ethereal oils from plants (see e.g. Peng et al., 2004, J. Chromatogr. A., 1040:1-17; Eikani et al., 2006, J. Food Eng., 80: 735-740; Durling et al., 2006, Food Chem., 101:1417-1424). For distillation raw plant material e.g. leaves, roots, flowers, fruit peel, etc. is placed into a distillation apparatus above water and heated. The steam vaporizes the volatiles, and the vapor is condensed and collected. The distillate can then be fractionated further (e.g. by solvent extraction) or enriched for specific compounds. Alternatively, the starting material comprises mainly the volatile to be purified.

Solvent extraction from tissues uses for example hexane or supercritical carbon dioxide and/or ethyl alcohol to extract the volatiles, optionally in combination with distillation steps. Headspace volatiles may also be extracted using solvents, such as pentane ether.

As preferably relatively pure compounds are used, i.e. compounds free of plant tissue, waxes, resins or other plant-derived contaminants, as well as substantially free of non-desired terpenes, it is preferred to use synthetic compounds and/or recombinantly produced compounds and/or substantially purified compounds. Thus in one embodiment of the invention, each of the individual compounds is "substantially pure", whereby less than 10%, more preferably less than 5%, preferably less than 3%, 2% or 1% of contaminants, such as non-desired hydrocarbons, proteins, waxes, resins, DNA, RNA, sugars, cell walls, or other plant-components, are present.

The compounds can be also be obtained from commercial suppliers, such as Sigma-Aldrich (see www.sigmaaldrich.com). For example, beta-myrcene (Sigma-Aldrich product no: 64643, ≥95% purity), para-cymene (Sigma-Aldrich product no: 30039, ≥99.5% purity) and gamma-terpinene (Sigma-Aldrich product no: 86476, ≥98.5% purity) are available from Sigma-Aldrich, as is (+)-limonene and (−)-limonene or both enantiomeres (Sigma-Aldrich product no: 62118, 62128, 89188) and $(+)_2$-carene (Sigma-Aldrich product no: 21984), alpha-phellandrene (Sigma-Aldrich product number 77429, ≥95% purity) and alpha-terpinene (Sigma-Aldrich product no: 88473, ≥95% purity). Zingiberene and curcumene can also be isolated from ginger oil, e.g. by chemical modification and subsequent distillation as described by Millar (1998, J. Nat. Proc. 61: 1025-1026). Compounds, such as beta-phellandrene, can be synthesized chemically de novo (see e.g. U.S. Pat. No. 4,136,126).

It is also possible to produce the above monoterpene and/or sesquiterpene compounds in recombinant microorganisms, such as bacteria (e.g. *E. coli*) or fungi (e.g. yeasts, such as *Pichia* or *Hansenula*). The expression of one or more genes in microorganisms, preferably with secretion of the compound into the growth medium, allows larger quantities and cheaper production of pure compounds (free of other monoterpenes and sesquiterpenes) to be made. For example WO2006/065126 describes terpene hydroxylation, whereby e.g. limonene can be produced from suitable substrates in microbial hosts expressing a cytochrome P450 enzyme. See also Reiling et al. (Biotechnol. Bioeng. 2004, 87: 200-212), describing production of mono- and di-terpenes in *E. coli*.

The compounds and/or compositions comprising, or consisting of, one or more of these may be in the form of a volatile/gas, a liquid, a semi-solid (e.g. gel beads, creams, foams, etc.) or as a solid (granules, powders, etc.). They may, thus contain an inert carrier, such as a solvent, for example an alcohol (e.g. ethanol) or ether (e.g. pentane ether) or another organic solvent (e.g. hexane), which does preferably not have any effect on whitefly behavior. Instead of being dissolved in a solvent, such as alcohol or alcohol mixture or ether, also oil-based carriers may be used. Water is generally not a very suitable carrier, as miscibility of these lipophilic compounds in water is low or absent. The formulation of the compound(s) should be in such a way that it is easily applied to the target location and that the insect behavior is affected (and preferably that the insect distribution in the applied area is significantly affected). The repellent compounds and/or compositions are in one embodiment applied to a plurality of crop plants, while the attractant compositions are preferably applied to a location distinct from the crop plants, e.g. a boarder trap-crop or trap rows, interplanted between with the crop rows. When applied to plants, e.g. in the field or in greenhouses, a gas, liquid (e.g. which evaporates upon contact with air) or semi-solid form may be preferred, which can be sprayed or dispersed onto the aerial plant surface. Solid formulations include granules, powders, slow-release matrices (e.g. coatings or matrices surrounding the active ingredient and releasing the ingredient slowly), etc. The active ingredient and carrier (e.g. the solvent) may also be placed into a solid container, such as rubber septa (commercially available), from which the volatiles are released slowly.

However, all types of formulations are envisaged herein for both the attractant-formulations and the repellent-formulations according to the invention. The skilled person will know how to make an appropriate formulation, taking the following factors into consideration: 1. percent of active ingredient, 2. ease in handling and mixing, 3. safety for humans and non-target animals (such as insect pest predators or parasites), 4.

environment where the formulation is to be applied (field, greenhouse, etc.), 5. habits of the target insect (e.g. whiteflies and/or other insect pests), 6. the crop to be protected and possible injury to the crop. Generally, formulations suitable for plant pesticides can be used or adapted for making a repellent- or attractant formulations according to the invention. Types of formulations include the following:

a) Emulsified Concentrates (EC) formulations, which are liquid formulations wherein the active ingredient(s) is/are dissolved in oil or another solvent and wherein an emulsifier is added so that the formulation can be mixed with oil or water for spraying.

b) High concentrate liquids, spray concentrates and ULV's (ultra low volume concentrates), which contain high concentrations of active ingredient(s) and are generally diluted by mixing with oil or water, or are used without dilution directly.

c) Low concentrate liquids or oil solutions, which generally require no further dilution and comprise the active ingredient(s) in the appropriate application dosage.

d) Flowable liquids can be made for active ingredients that do not dissolve well in water or oil. The active ingredient is a solid, which is ground or in fine powder form. The fine solid is then suspended in liquid (together with suspending agents, adjuvants and/or other ingredients).

e) Solutions, or water soluble concentrates, which are liquid formulations, made by dissolving the active ingredient(s) in a solvent (e.g. water or organic solvents).

f) Encapsulated formulations, whereby the active ingredient/s is/are contained in small capsules or coatings, which in turn can be for example suspended in a liquid (e.g. to be sprayed).

g) Dust formulations, which are applied dry. They include the active ingredient(s) as solid, e.g. finely ground, optionally mixed with other powders, such as talc, etc.

h) Granules, which are made of dry, porous material to which the active ingredients have been applied. Often granule formulations are applied to the soil, but they can also be applied to the plants.

i) Wettable powders, which are dry, powdered formulations. In contrast to Dust formulations, wetting agents and/or dispersing agents are present in the formulation. Often they contain higher concentrations of active ingredients than Dust formulations, e.g. 15%-95% active ingredient.

j) Soluble powders, which are similar to wettable powders, but dissolve completely in solution.

k) Dry flowables, which look like granules, but are used in the same way as wettable powders.

l) Liquefied gas and/or fumigants, which are liquefied volatiles or gaseous formulations. Certain volatiles can form liquids e.g. under pressure, and will turn into vapors (volatiles) again under certain conditions, e.g. once the pressure is released. The vaporized active ingredient (volatile) will have the desired effect upon release. The formulations may be released into the soil or under coverings, such as tarps (canvases), or into (relatively) closed environments. The (liquefied or gaseous) active ingredient may also be incorporated into capsules, gels or other matrices which slowly release the vaporized active ingredient into the atmosphere.

m) Bait formulations refer to formulations which contain one or more attractant compounds according to the invention. Optionally, they may contain other attractants or even compounds toxic to the target insect species and/or to other insect species, for example they may contain one or more insecticides, which kill the target insect (and/or other insects), e.g. the whiteflies, when ingested or upon contact. Such toxins need not be contained in the attractant formulation as such, but can also be applied to the target area or target plants as a separate component (e.g. before, after or together with the attractant compound or composition). Such a kit of compositions is also an embodiment of the invention.

n) Aerosols are gaseous formulations stored under pressure, e.g. in a can.

Formulations under 1) above are especially preferred herein.

Formulations may also be similar to those used for the insect repellent DEET™ (N,N-diethyl-m-toluamide or N,N-diethyl-3-methylbenzamide), especially when mammalian disease vectors are to be repelled. DEET™ is available in >200 formulations, such as aerosol sprays, non-aerosol sprays, creams, lotions, foams, sticks, controlled release formulations (encapsulated in protein), etc., with the active ingredient ranging from 4-100%. See also U.S. Pat. No. 4,774,082 and U.S. Pat. No. 6,180,127 for volatile insect repellent formulations and slow release formulations.

Similarly, formulations as commonly used for volatile herbicides (e.g. volatile ester herbicides) may be used herein see e.g. U.S. Pat. No. 3,725,031 or Day, Weed Research, Volume 1, Issue 3, Page 177-183, September 1961, describing volatile, leaf applied, formulations of Dalapon to reduce soil contamination.

Optionally other components may be added to the active ingredient (the repellent(s) or attractant(s)), such as nutrients, osmotic agents, one or more suitable carriers, diluents, emulsifiers, wetting agents, surfactants, dispersants, adjuvants, volatiles, stabilizers, etc. "Carrier" refers to compounds which are combined with the active ingredient(s) but which themselves have no significant biological activity, at least not on the target insect species, such as whiteflies. Preferably, the carriers used have also no negative biological effects on plants, e.g. the host crop, i.e. they preferably have no, or minimal, phytotoxicity. Carriers may be gases, liquids (e.g. volatile liquids) or solids and they may be water, oil, oil-comprising solutions (e.g. emulsions), solvents, etc.

The percentage of active ingredient in the final attractant or repellent composition may vary considerably, depending on the activity of the active ingredient(s), the type of formulation, site and mode of application, etc. The percentage of active ingredient(s) may thus be at least about 1%, 2%, 5%, 10%, 30%, 50%, 70%, 80%, 90%, 95% or even 100% weight per volume of the composition.

Thus, a composition comprising one or more active ingredients (one or more repellents or one or more attractants) can be applied to the plants or area to be treated e.g. by spraying or by vaporisation from a carrier. Also, repellent compositions can be placed (e.g. on carriers) in between the plants while the composition comprising or consisting of one or more attractants are preferably placed in/on traps or in/on locations nearby the plants which are to be protected.

The compositions according to the invention may also comprise other biologically active compounds, such as other insect attractants or repellents known in the art, insecticides, etc. Also, different stages of the target insect may be more susceptible to one compound than to another, and compounds (according to the invention and/or compounds known in the art) which target different stages of a pest species may be combined. Similarly, different pest species may be targeted by combining effective amounts of compounds (according to the invention and/or compounds known in the art) for each of the pest species.

Repellent or attractant compositions may further comprise insecticides, herbicides (if the host plant to be treated is herbicide resistant, e.g. transgenic herbicide resistant plants), fungicides and/or other biologically active ingredients, such as growth enhancing agents, safeners, fertilizers, etc.

Insect attractants compositions may also contain one or more insecticides in order to kill insect survival and/or reproduction. Also insect pheromones, which attract the target insect (e.g. whiteflies), may be added to the attractant compositions. Similarly, attractants of predators of the target insect(s) may be comprised in the compositions.

Preferably, the compositions do not contain substances which have negative biological effects on plants (e.g. the host crop or trap plant), i.e. they preferably have no, or minimal, phytotoxicity on host- and/or trap-plant species. Phytotoxicity of individual components or compositions can be easily tested by contacting the components or composition with plant tissue, e.g. leaves. Also, the compositions preferably have no negative effect on non-target insects, such as predators of whitefly.

An effective amount for attracting or repelling the target pest, e.g. whiteflies, should be present in the composition. Suitable amounts are provided (especially for whiteflies, but not limited thereto) in Table 2, below. Suitable amounts may range from at least about 0.5, 1, 2, 3, 4 or 5 µg volatile compound released in 24 h to at least about 10, 20, 30, 50, 100, 200, 300, 400, 500, 600, 800, 900 or 1000 µs or more of the volatile compound being released per 24 hours, or equivalents thereof. Suitable amounts may also be expressed as amounts per kg biomass (fresh weight) to be treated, and range from e.g. at least about 0.01 mg compound per kg biomass per 24 hours to at least about 60, 70, 80, 90 or 100 mg compound per kg biomass to be treated per 24 hours. For example, effective amounts include at least about 0.05 mg/kg/24 h, 0.1, 0.2, 0.5, 1.0, 2.0, 3.0, 4.0, 5.0, 6.0 7.0, 8.0, 9.0, 10, 15, 20, 30, 40, 50 mg/kg/24 h, or more; see also Table 2 for non-limiting examples. For other insect pests, different amounts may be required, which can however be tested without undue experimentation, using for example bioassays. Thus, the effective amount can be determined experimentally, using undue experimentation. It may vary, depending on the formulation and application area. A greenhouse (closed environment) may require lower amounts than a field environment. Importantly, the number of target pests, such as whiteflies, actually probing the plant tissue contacted with a composition comprising or consisting of a repellent is significantly reduced compared to the untreated control plants, whereby the virus transmission and virus damage is reduced on the treated plants.

TABLE 2 suitable amounts of insect repellents or attractants, especially for whiteflies

| volatile compound (common name) | active compound per 24 h per kg biomass (FW) to be treated |
|---|---|
| repellents | |
| alpha-curcumene | 1-30 mg, e.g. 1.4-28 mg |
| beta-myrcene | 0.05-5 mg, e.g. 0.1-2 mg |
| para-cymene | 0.05-3 mg, e.g. 0.05-1 mg |
| gamma-terpinene | 0.1-10 mg, e.g. 0.4-8 mg |
| zingiberene | 1-60 mg, e.g. 2.8-55 mg |
| alpha-terpinene | 0.1-10 mg, eg. 0.5-8 mg |
| alpha-phellandrene | 0.01-2 mg, e.g. 0.06-1.5 mg |

TABLE 2-continued suitable amounts of insect repellents or attractants, especially for whiteflies

| volatile compound (common name) | active compound per 24 h per kg biomass (FW) to be treated |
|---|---|
| attractants | |
| beta-phellandrene | 0.1-10 mg, e.g. 0.4-8 mg |
| limonene | 0.05-5 mg, e.g. 0.05-2 mg |
| 2-carene | 0.05-3 mg, e.g. 0.05-1 mg |

FW = Fresh weight

In one embodiment the composition comprising, or consisting of, one or more repellent compounds simulates the concentrations and/or compound ratios as measured in different, unattractive (repellent) wild tomato plants (see Table 3 below), but lack other terpene and/or terpenene compounds found naturally in such plants.

TABLE 3

Ratio of effective compounds

| tomato line | effective compounds in mixture | ratio |
|---|---|---|
| Repellents | | |
| LA2560 | p-cymene:gamma-terpinene:beta-myrcene | 1:1:4 |
| PI27826 | zingiberene:curcumene | 1:1.3 |
| LA716 | p-cymene:gamma-terpinene:zingiberene | 1:1:18 |
| LA1340 | p-cymene:gamma-terpinene:beta-myrcene | 1:0.8:4 |
| Attractants | | |
| S. lycopersicum | beta-phellandrene:limonene:2-carene | 1:2.4:0.2 |

Obviously, other amounts and other ratios than those presented in Tables 2 and 3 above may be suitably used, e.g. for other insects or insect-host combinations. The most suitable amounts and/or ratios can be determined by the skilled person without undue burden, using for example bioassays (see below) or field assays.

Whether an amount of one or more active ingredients is an "effective amount" for attracting or repelling the target pest (e.g. whiteflies) can be easily tested. For example, the following bioassay may be used for whiteflies and/or other target pests. Obviously, similar bioassays can be devised by the skilled person.

A suitable bioassay involves, for example, the following steps:

(a) providing a plurality of host plants, e.g. tomato cultivars;
(b) contacting the plants, either directly or indirectly, with one or more compounds and/or with one or more concentrations of a compound or compound-mixture (or compositions comprising these). Indirect contact may be effected by including a support, such as rubber septa (e.g. Sigma Aldrich Z167258) or filter paper disks, to which the compound(s) have been added, on or near the plants. For example, rubber septa loaded with one or more volatile compounds may be added to plants (the 'treated' plants) but not to the controls (the control or reference plants, or 'untreated' plants). Reference plants are either contacted with a control composition (e.g. lacking the active ingredient/s) or are not contacted with the compound(s)/composition(s);
(c) releasing the target insect into the area of the treated and untreated plants and allowing the insects to settle on the plants; preferably the target insects are released in such a way that no bias towards the treated or untreated/controls results from the release itself; also, it is preferred that other cues which could affect insect behaviour (such as visual cues) are reduced or eliminated, so that the landing, probing and/or feeding of the insects on the treated and untreated/control plants is not influenced (or influenced as little as possible) by other cues;

(d) analyzing the plant preference of the insects at one or more time-points after release (e.g. at 10, 20, 40, 60 minutes, or more, after release) and comparing the number of insects on the treated plants with the number on the untreated plants.

The data is preferably analyzed statistically in order to determine whether one or more compounds have an attractant or repellent effect or what the most optimal concentration of an attractant or repellent compound or compound-mixture is. See also the Examples for a suitable bioassay for whiteflies.

Depending on the insect species, the experimental setup may be varied slightly. For whiteflies, for example, preferably at least 50, 100, 150 or more whiteflies are given a choice between treated and untreated/control plants.

Uses According to the Invention

The invention provides the use of one or more of alpha-curcumene, beta-myrcene, para-cymene, gamma-terpinene, alpha-terpinene, alpha phellandrine and/or zingiberene for the preparation of an insect repellent composition, preferably a sap-sucking insect pest repellent composition, most preferably a whitefly repellent composition.

In another embodiment the invention provides the use of one or more of beta-phellandrene, limonene and/or 2-carene for the preparation of an insect attractant composition, preferably a sap-sucking insect pest attractant composition, most preferably a whitefly attractant composition.

In yet a further embodiment the use of one or more of the above repellent or attractant compositions for repelling or attracting mammalian insect pests, such as mosquitoes (e.g. malaria mosquitoes, yellow fever mosquitoes, and the like), is provided herein. Other mammalian insect pests include, for example, the Scottish biting midge or other blood-sucking midges. Such compositions, especially repellents, can be used as sprays, creams, solutions, etc. to be applied to e.g. the skin, clothes, fabrics, areas outdoors or indoors, etc. in order to exert their effect. Especially mosquito repellents and/or midge repellants are provided, which comprise or consist of an effective amount of one or more of the seven compounds of Table 1. Following application to the skin or clothes, or to environment (e.g. as an aerosol) where the humans or animals want to reside, or to a carrier or support the number of mosquitoes (especially female mosquitoes) is significantly reduced compared to an untreated control.

The methods for determining the effective amount of one or more compounds and/or compositions are analogous to those used for plant pests. For example, an analogous assay can be used, comprising e.g. choice assays, whereby the insects are placed into Y-shaped tubes and allowed to move upwind along either branch of the Y. In one tube the repellant or attractant compound is placed and the number of insects making a specific choice is counted. In vivo tests may include (a) providing a plurality of mammalian subjects;
(b) contacting the subjects, either directly or indirectly, with one or more compounds and/or with one or more concentrations of a compound or compound-mixture (or compositions comprising these). Indirect contact may be effected by adding the compound or composition to clothing. Reference subjects are either contacted with a control composition (e.g. lacking the active ingredient/s) or are not contacted with the compound(s)/composition(s);
(c) releasing the target insect into the area of the treated and untreated subject (or part thereof (e.g. the arm or hand) and allowing the insects to settle.
(d) analyzing the number of bites of the insects at one or more time-points after release (e.g. at 5, 10, 20, 40, 60 minutes, or more, after release) and comparing the number of insects on the treated subjects with the number on the untreated subjects.

Parts of the invention described for plant insect pests thus apply in an analogous way to mammalian insect pests and where "plant insect pests" are referred to, mammalian insect pests are encompassed analogously, with obvious variations (e.g. support material is preferably clothing, or containers, such as spray-containers, lotion containers, and the like).

The compositions may be used according to the methods described further below.

Support Materials Comprising Attractant Compounds or Compositions

In another embodiment the invention provides the use of one or more of beta-phellandrene, limonene and/or 2-carene for the preparation of a support material comprising an insect pest (e.g. whitefly) attractant composition. The support material comprising an attractant compound or composition according to the invention is also an embodiment of the invention per se. The material is preferably a container, holder or other solid support onto or into which the attractant composition is placed. The solid material may be a trap, such as known insect traps. Alternatively, the solid material may be a volatile-dispenser, as described above. The support material may also be a trap plant or a plurality of trap plants, or parts thereof (e.g. a leaf). Preferred trap plants are plant species and/or varieties which are susceptible to the target insect (e.g. whiteflies) and which are natural hosts of the target insect pest species. For example, cultivated tomato species can be used, whereby the attractant is applied onto the aerial plant material. Alternatively, materials comprising the attractant (e.g. rubber septa or filter papers) may be added to the plants or between the plants, so that potential phytotoxic effects of the compositions are avoided. By adding the compounds or compositions to the support material, direct contact between the compound or composition and the plant tissue is avoided.

Any support material may be used. The solid material may, thus, for example be a filter paper (onto which the attractant/s is/are applied by e.g. spotting, spraying or dipping) or a rubber or synthetic material, such as rubber septa. The solid material may be made of plastic, solid synthetic material, polymers, metal, glass, paper, carton, biological material (e.g. wood, cork, etc.), or the like. It may be in the form of tubes, disks, blocks, boxes, cubes, beads, (nano)particles or granules, or any other. Suitable rubber septa are for example available from Sigma-Aldrich (Z167258). Semi-solid support materials may be gels (e.g. agar), foams or creams.

Support Materials Comprising Repellent Compounds or Compositions

In yet another embodiment the invention provides the use of one or more of alpha-curcumene, beta-myrcene, para-cymene, gamma-terpinene, alpha-terpinene, alpha-phellandrene and/or zingiberene for the preparation of a support material comprising an insect pest (e.g. whitefly) repellent composition. The support material comprising a repellent compound or composition according to the invention is also an embodiment of the invention per se. The material may be a container or other solid material onto or into which the repellent composition is placed. The solid material may be a slow release material, such as a gel or other matrix or container, which emits the volatiles slowly, over a longer period. For example, solid material may be a volatile dispenser, as described above. The material may also be a crop plant or a plurality of crop plants. Preferred crop plants are plant species and/or varieties which are to be protected from target insect pest (e.g. whitefly) damage. For example, cultivated host species, such as tomato, cotton, Curcubitaceae, potato, etc. can be protected from insect pest (e.g. whitefly) damage by applying the repellent onto the aerial plant material or within the planted field, e.g. on carriers or dispensers placed at regular intervals throughout the field. Supports comprising the repellent (e.g. rubber septa or filter papers) may be added to one or more of the crop plants or between the plants, so that potential phytotoxic effects of the compositions are avoided. By adding the compounds or compositions to the support material, direct contact between the compound or composition and the plant tissue is avoided.

Any support material may be used, as described above for attractant supports.

See also the methods herein below.

Methods for Repelling and/or Attracting Insect Pests Using Compounds or Compositions According to the Invention A method for reducing infestation of cultivated plants by insect pests, i.e. a method for repelling and/or attracting insect pests such as whiteflies and/or other insect pests, is provided, comprising the steps of:
(a) providing a composition comprising or consisting of one or more repellent compounds selected from S-curcumene, beta-myrcene, para-cymene, gamma-terpinene, alpha-terpinene, alpha-phellandrene and/or zingiberene; and
(b) adding said composition one or more times to a plurality of crop plants; and/or
(c) providing a composition comprising or consisting of one or more attractant compounds selected from beta-phellandrene, limonene and/or 2-carene, and
(d) adding said composition one or more times to one or more trap plants or trap materials.

The compositions under (a) and (c) are described herein above. Optionally, steps (a) and (b) may be repeated several times. Likewise, optionally steps (c) and (d) may be repeated several times. It is clear that, when protection of a crop is desired, attractant compositions may be used separately from repellent compositions, and vice verca, or both may be used together, to e.g. repel insects from the crop and attract insects to the trap, which may for example be located near the crop or interspersed with the crop. Thus, in essence three methods are provided: (a) protection of the crop by repelling insect pests, (b) protection of the crop by attracting insect pests away from the crop plants and (c) using both strategies together for reducing insect infestation of the crop.

In step (b) the compositions may be added directly to (contacted with) the crop plants or parts thereof, e.g. by spraying onto the plants, by spraying individual plants or leaves or by spot application to individual leaves, by fumigation, by manual placement of liquid, solid or semisolid formulations onto a plurality of plants or plant parts, by dusting etc. "Direct contact" (i.e. physical contact) between the plant material and the compounds or compositions can, thus, be used.

Alternatively, in another embodiment, "indirect contact" between the crop plants and the compounds or compositions is used, whereby the composition or compound is brought into contact with a support (or carrier) material first, and said support material (comprising said compounds or compositions) is then placed either onto one or more plants or plant parts, or near the plants, e.g. between rows, between plants or into/onto the soil where the plants are growing or are to be grown.

The best place of application of the repellents on or near the host crop, as well as the frequency of application, depend on a number of factors, such as the architecture and physiology of the crop, the age of the crop, the formulation, the insect pest infestation in the area, etc. For formulations which become volatile very quickly, a more frequent application may be required to effectively repel the target insect pests, e.g. whiteflies. Similarly, in areas with lots of rainfall, an aerial application may be washed off more quickly, requiring one or more further applications or shorter intervals of applications. The skilled person can easily determine the optimal application frequency for sufficiently reducing infestation. Application may, thus be one or more times daily, weekly or monthly or even as low as 1, 2, 3 or 4 times per growing season of the crop. In one embodiment the composition comprising one or more repellent compounds according to the invention may also be applied to the area where the crop is to be grown prior to seeding or planting of the crop, so that infestation is already reduced before emergence of the seedlings.

Suitable application frequencies may, thus, for example be 1, 2, 3, 4 or more times between planting and harvest of the crop. The crop may be grown in a closed environment (e.g. a greenhouse or tunnel), a semi-closed environment (e.g. a field crop covered by canvas) or an open environment. Crops which benefit from the attractant and/or repellent compositions according to the invention are of course crops which are natural hosts to the susceptible insect pests, whose behaviour is altered by the compounds and compositions described herein. In one embodiment the crop plants are therefore plant species which are hosts of sap-sucking insects, in particular whitefly. The greenhouse whitefly, *Trialeurodes vaporariorum*, has a very broad range of host species, such as most vegetable species and ornamentals. The silverleaf and sweet potato whitefly (*Bemisia argentifolii* and *B. tabaci*) also have a very broad host range, including most vegetable species.

In a preferred embodiment the crop plants are tomato plants, preferably cultivated tomato. The crop plant may also be a genetically modified plant, i.e. a transgenic or cisgenic plant, comprising e.g. a herbicide resistance gene.

Application of the repellent-comprising compositions preferably significantly reduces virus transmission, due to the reduction of adult sap-sucking pests, such as whiteflies, and plant tissue probing in the treated crop. A significant reduction in virus transmission in the treated crop compared to an untreated crop can, therefore, also be used as a measure of efficacy of the treatment. Alternatively, the number of target insects (e.g. whiteflies) can be counted/estimated, or yield and/or quality of the crop can be compared between treated and untreated crops in order to determine the most effective dosage and application-regime of any of the compositions according to the invention.

One need not apply the same repellent composition two or more times to the same crop, but an alteration of treatments is also envisaged, as is a combination of treatments. For example, a treatment with a composition comprising (or consisting of) one of the seven repellents may be altered with, or combined with, a treatment with a composition comprising (or consisting of) any one of the other seven repellent compounds. Similarly, a treatment with a composition comprising (or consisting of) two of the seven repellents may be altered or combined with a treatment with a composition comprising (or consisting of) any one of the other seven repellent compounds, or consisting of two other repellent compounds, etc. Thus, in step (a) one may also provide several different compositions, which may then be applied in step (b), either together at the same time, or consecutively.

Similarly, the formulation and/or concentration of the active ingredient(s) provided in (a) and applied in (b) need not be the same. One can, for example increase or decrease the concentration of the active ingredient throughout the growing season of the crop, e.g. depending on insect pest (e.g. whitefly) infestation or warnings thereof.

In one embodiment, however, the active ingredient(s) provided in (a) and applied in (b) is/are chemically the same, and are preferably also in the same formulation and/or concentration.

In a preferred embodiment, the active ingredient(s) is/are slowly released from the composition over a longer period of time. A preferred formulation is, therefore, a slow release, or controlled release, formulation. Such formulations can be made using methods known in the art, for example for pesticides, using (micro)encapsulation, laminated strips, polyvinylchloride strips, rubber pellets, etc. or other methods for slow and/or controlled release. See e.g. Barlow, F (1985, Chemistry and formulation. In: Pesticide Application: Principles and Practice. Ed: P T Haskell. Oxford Science Publications: Oxford. pp 1-34), Dent, D R (1995, Integrated Pest Management. Chapman & Hall: London, Glasgow, Weinheim, N.Y., Todyo, Melbourne, Madras), Rombke, J & J M Moltmann (1995, Applied Ecotoxicology. Lewis Publishers: Boca Raton, N.Y., London, Tokyo) or Ware, G W (1991, Fundamentals of Pesticides. A self-instruction guide. Thomsom Publications: Fresno USA).

The treatment of the crop with repellents may be combined with the treatment of plants or areas near the crop with attractants or bait compositions. Alternatively, the use of attractants or bait compositions may in itself be sufficient to protect the crop from insect pest (e.g. whitefly) damage, and in such cases no treatment of the crop itself is necessary.

The above descriptions for steps (a) and (b) apply also to steps (c) and (d), with the difference that in step (d) the plants need not be crop plants and need not even be of the same species as the crop plant (although they may be). The trap plants may be any species of plant, but preferably they are plants naturally susceptible to the insect pest (e.g. whiteflies).

The plants may be grown near the crop in order to lure the insects from the crop, thereby reducing infestation of the crop. For example, strips or boarders of trap plants may be grown around one or more edges of the crop plants. Alternatively, crop plants and trap plants may be grown in parallel rows. Obviously, it is also possible to grow the trap plants in distinct areas within the crop plants, e.g. in the middle of the crop field.

The same also applies to trap materials, which may be interspersed near or within a crop field or green house-grown plants. It is preferred that the trap plants or trap materials are near enough to the crop plants to lure the whiteflies away from the crop plants. The trap materials may be traditional insect traps to which the compositions according to the invention are added.

FIGURE LEGENDS

Figure 1B:
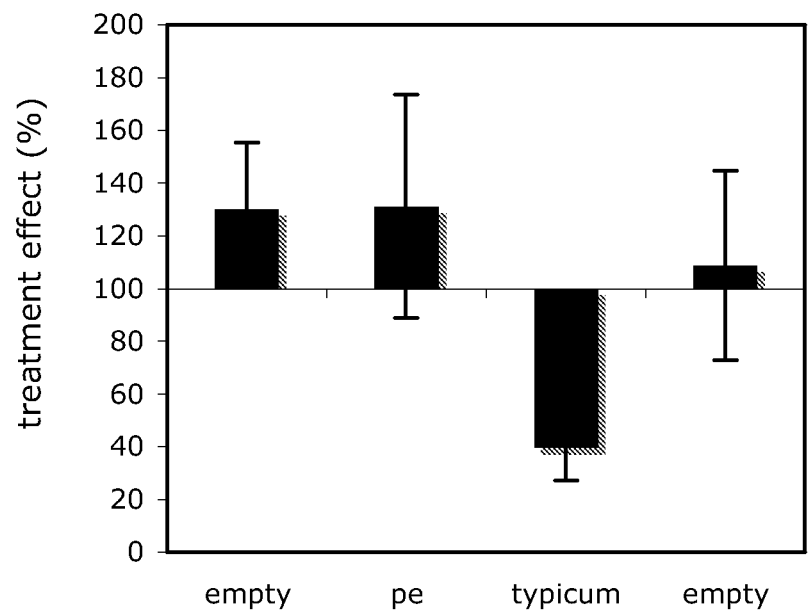

FIG. 1:
Treatment effect of wild-tomato headspace to one plant in a setup of four *S. lycopersicum* plants (expressed as % of untreated setup). empty: empty carriers; pe: carriers containing pentane:ether; pennelli: carriers containing total headspace (collected over 24 h) of *S. pennelli*; typicum: carriers containing total headspace (collected over 24 h) of *S. habrochaites f. typicum*. Bars present averages of 3 experiments (±SE).

FIG. 2:
Treatment effect of a volatile compound (or mix) to one plant in a setup of four *S. lycopersicum* plants (expressed as % of untreated setup). A) treatment with p-cymene; B) treatment with γ-terpinene; C) treatment with β-myrcene; D) treatment with mix of p-cymene, γ-terpinene and β-myrcene ("mix"); E) treatment with α-terpinene; F) treatment with α-phellandrene; G) treatment with epizingiberene; H) treatment with S-curcumene; I) treatment with zingiberene; J) treatment with R-curcumene. Bars are averages of 8 experiments (±SE). nt: plants in set up to which no volatiles were added.

Figure 3:
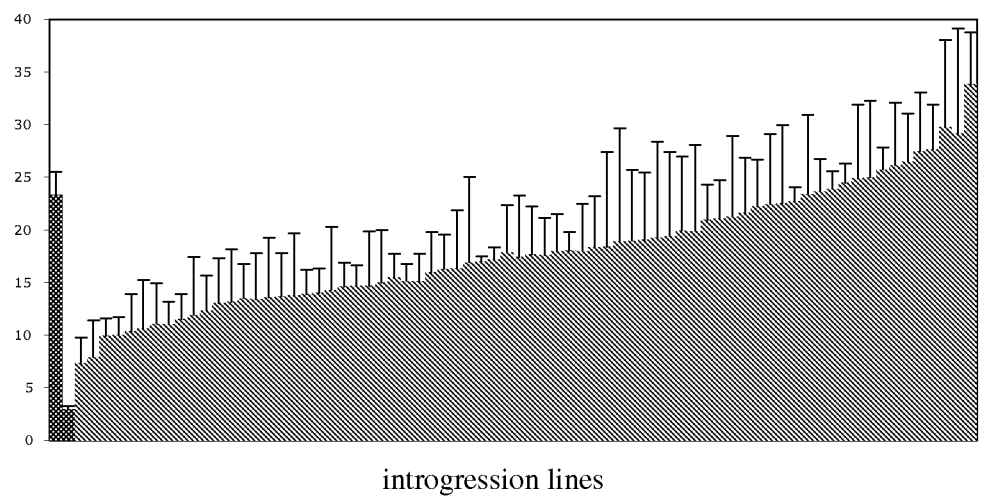

FIG. 3:
Relative *B. tabaci* attraction (%) to 72 introgression-lines (*S. lycopersicum* cv Moneyberg×*S. pennelli* LA716) (light bars) compared to both parents (dark bars; Moneyberg and LA716 respectively). n=3±SE.

The following non-limiting Examples illustrate the different embodiments of the invention. Unless stated otherwise in the Examples, standard protocols known in the art are used.

EXAMPLES

Example 1

Tomato Head-Space Volatiles and Whitefly Preferences 1.1 Material and Methods

A population of *Bemisia tabaci* was collected at a common greenhouse in Santa Maria del Aguila (Almeria, Spain) in October 2005. By PCR analyses this population was identified to belong to the Q-biotype. The population was reared in a climate chamber (Temperature 28° C., 16 h light) on a mixture of tomato and cucumber plants. Preference of the insects for particular plants (treated or untreated/control-treated) was tested in free choice bioassays.

It is known that whiteflies make use of both visual cues as well as smell to find their host. It was shown by the inventors that *B. tabaci* can differentiate between different tomatoes using volatile cues by omitting visual cues in a 'blind' assay where tomatoes were placed under a mesh cover.

In order to test the effect of scent of the tomato plant on host-preference of the whitefly the sampled headspace, containing the full blend of semiochemicals, of the more repellent (as previously established by the inventors) wild-tomato plants accessions LA716 (*S. pennelli*), PI27826 (*S. habrochaites f. typicum*) and PI126449 (*S. habrochaites f. glabratum*) was applied to a non-repellent/attractive plant (cv Moneymaker). The seeds were obtained either from 1) the C.M. Rick Tomato Genetic Resource Center (TGCR), Department of Plant Sciences, University of California-Davis, One Shields Avenue, Davis, Calif. 95616, United States of America, or from 2) The United States Department of Agriculture—Agricultural Research Service, Plant Genetic Resources Unit, Cornell University, 630 West North Street, Geneva, N.Y. 14456, United States of America.

Tomato Headspace Sampling

Volatiles were collected by placing three week old wild-tomato plants in a climatised room in large desiccators for 24 hours, including a 16 h day period. Desiccators were ventilated with carbon-filtered pressure-air at 400 ml min$^{-1}$. Volatiles were captured on a sampling tube containing 300 mg Tenax resin according to Kant et al., (2004). Next, volatiles were eluted off the Tenax with 1 ml pentane:diethylether (4:1). including BA as an internal standard. Identification was achieved by injecting 1 µl of the eluent into an Optic injection port (ATAS GL International, Zoeterwoude, Nl) at 50° C. which was heated to 275° C. at a rate of 4° C./s/The split flow was 0 ml for 2 minutes and then 25 ml min$^{-1}$. Compounds were separated on a capillary DB-5 column (10×180 µm, film thickness 0.18 µm; Hewlett Packard) at 40° C. for 3 min and then to 250° C. at 30° C. min$^{-1}$ with helium as a carrier gas. The column flow was 3 ml min$^{-1}$ for 2 minutes and 1.5 ml min-1 thereafter. Mass spectra of eluting compounds were generated at 70 eV (ion source at 200° C.) and collected on a Time-of-Flight MS (Leco Pegasus III, St. Joseph, Mich., USA) with a 90 sec acquisition delay at 1597 eV, at an acquisition rate of 20 spectra sec$^{-1}$.

Sample identification and quantification was based on synthetic external standards of known concentration (Fluka, Mich., USA). Each tomato accession was measured 6 times. Additionally, a 1 ml sample (pentane-diethylether containing tomato volatiles) was used to impregnate filterpaper cards (Whatman, 25 mm diameter) to be used in bioassays with *B. tabaci*.

Free-Choice Bioassays with *B. tabaci* and Tomato

Free choice experiments with *B. tabaci* were carried out in a greenhouse compartment (28° C., RH 65%). Light was supplied by high-pressure sodium lamps (Hortilex Schréder SON-T PIA GP 600 W) with a radiation of 250 W/m$^2$. The preference behaviour of *B. tabaci* biotype Q (Almeria population) and biotype B (labculture Netherlands) was compared in bioassays with different wild tomatoes (LA1777, LA2560, GI1560) and *S. lycopersicum* cv Moneymaker). Plants were placed inside a plastic covered wooden tray (170×100×20 cm) filled with soil, at equal distance from each other. Two hundred adult whiteflies were captured, placed at 4° C. for five minutes and then released in the middle of the setup. Ten and 20 minutes after release, the number of whiteflies on each plant was recorded. Since no differential behaviour between *B. tabaci* B and Q was found, all further bioassays were done with the Almeria (Q) population.

For bioassays with headspace (total headspace or single compounds) four potted tomato plants (*S. esculentum* cv Moneymaker) were placed in a square setup at a distance of 50 cm. One hundred and fifty adult whiteflies were released and recorded as described above. To test the effect of selected headspace components on repellence, synthetic standards (FLUKA) were applied to either 10 filter-papers discs (Whatman, 25 mm diameter) or 10 rubber septa (Sigma Aldrich, Z167258). Prior to loading, the septa were placed in CH$_2$Cl$_2$ for 24 h and air-dried for 3 days (Heath et al., 1986). The paper discs or septa containing volatiles were attached to one of the four plants with metal wire. The position of the treated tomato was randomised. Five minutes after placing the volatiles on the plant, whiteflies were released. For each component at least 8 replications were carried out. Treatments were administered in a setup in which compounds were always added to the same plant in comparison to 3 plants with empty carriers. Prior to each assay with volatiles, the experiment was done with the 4 plants in an untreated setup, in the same position to allow comparison in the same background.

1.2 Results

Results are shown in FIG. 1. These assays showed that the tomato cultivar Moneymaker can be made up to 60% less attractive when the total headspace components that make up the scent of a more repellent tomato accession is added to the plant's headspace, compared to its background smell. Pentane-ether, the solvent in which the headspace was eluted, was shown not to have any effect on repellence/attraction.

Example 2

Determination of Headspace Components Involved in *B. tabaci* Repellence 2.1 Material and Methods.

A collection of 16 wild type and 5 cultivated tomatoes was put together (Table 4). For each of these cultivars the level of whitefly repellence was established in randomised hexagon setups in free choice bioassays in an open greenhouse. In each experiment 300 new naive, adult whiteflies (Almeria population) were released in the middle of 6, randomly chosen, plants Twenty minutes after release the number of flies on each plant was counted. Each setup was repeated 3 times after which the two least repellent plants were replaced by two new test plants. Stepwise sequential testing finally resulted in a ranking into 7 classes with a clear differential repellence (Table 4).

The headspace of 16 wild tomatoes and 5 cultivated tomatoes (Table 4) was collected. Undisturbed 3-weeks old tomato plants were transferred to 40-L desiccators. The headspace was sampled during 24 h including a 16 h light period, by trapping of the volatile components as described above. The GC-MS analysis resulted in a unique 'fingerprint' of volatile components for each of the tomato accessions. Each accession was sampled 6 times.

2.2 Statistical Analysis

In a statistical analysis the correlation between the identified components of the tomato headspace and the ranking of whitefly repellence measured in the bioassays was made. Using two approaches, a stepwise-linear regression analysis and a MANOVA, 8 volatiles were identified to be correlated to whitefly repellence, whereas 24 other volatile compounds were eliminated as non-relevant for repellency or attraction.

2.3 Results

TABLE 4

Repellence ranking of 16 wild and 5 cultivated tomato accessions to *B. tabaci*, on a scale of 1-7, whereby 1 refers to highest repellent and 7 refers to least repellent/most attractant.

| tomato | accession | rank |
|---|---|---|
| *S. pennelli* | LA716 | 2 |
|  | LA1340 | 2 |
|  | LA2560 | 1 |
| *S. habrochaites* | LA1777 | 3 |
| *f. typicum* | PI27826 | 1 |
|  | PI27827 | 3 |
|  | LA1353 | 3 |
| *S. habrochaites* | PI126449 | 4 |
| *f. glabratum* | PI134417 | 3 |
|  | PI134418 | 4 |
|  | PI251304 | 3 |
|  | IVT701631 | 4 |
|  | LA407 | 5 |
|  | GI1560 | 3 |
|  | LA1840 | 5 |
| *S. peruvianum* | LA1708 | 5 |
| *S. lycopersicum* | cv Motelle | 6 |
|  | cv Mogeor | 6 |
|  | cv Monalbo | 6 |
|  | cv Moneymaker | 7 |
|  | cv Pitenza | 6 |

It can be seen from Table 4 that the headspace of cultivated tomato (cv) are the least repellent/most attractant to whitefly, while the headspace of wild tomato accessions is more repellent.

The compounds responsible for repellency or attraction of whitefly were identified and are shown in Table 5. Beta-myrcene, p-cymene, alpha-phellandrene, alpha-terpinene and gamma-terpinene are repellent compounds linked to *S. pennelli* whereas S-curcumene and 7-epizingiberene appear to be responsible for rendering the *S. habrochaites* (former typicum) more unattractive. Beta-phellandrene, limonene and 2-carene are significantly correlated to the more attractive cultivated *S. lycopersicum* plants.

TABLE 5

Identified semiochemicals associated to
B. tabaci repellence or attraction.

| source | terpenoid | association | behavioural effect | antennal response |
|---|---|---|---|---|
| S. pennelli | p-cymene | repellence | *** | 2.4 |
| S. pennelli | α-terpinene | repellence | * | 4.1 |
| S. pennelli | α-phellandrene | repellence | * | 2.2 |
| S. habrochaites f. typicum | 7-epi zingiberene | repellence | *** | 2.3 |
| S. habrochaites f. typicum | S-curcumene | repellence | ** | 5.0 |

Significance of effect on B. tabaci behaviour in choice-assays and responses of B. tabaci antennae to the various semiochemicals (mV)

TABLE 1

Accessions of wild tomato (S. pennelli, S. habrochaites and S. peruvianum) and cultivated tomato (S. lycopersicum) ranked based on relative repellence to B. tabaci.

| Tomato | Accession | rank | β-myrcene | p-cymene | γ-terpinene | curcumene | zingiberene | caryophyllene |
|---|---|---|---|---|---|---|---|---|
| S. pennelli | LA716 | 2 | — | 0.34 ± 0.13 | 4.01 ± 1.71 | 10.83 ± 8.29 | 68.5 ± 58.9 | 0.55 ± 0.20 |
|  | LA1340 | 2 | 1.46 ± 0.45 | 0.35 ± 0.11 | 2.49 ± 0.96 | 4.46 ± 4.35 | 6.56 ± 6.56 | 2.01 ± 0.82 |
|  | LA2560 | 1 | 1.36 ± 0.61 | 0.47 ± 0.18 | 5.88 ± 2.50 | 3.64 ± 3.09 | 8.44 ± 4.36 | 3.06 ± 1.50 |
| S. habrochaites (f. typicum) | LA1777 | 3 | 0.12 ± 0.10 | 0.05 ± 0.04 | 0.06 ± 0.07 | 12.3 ± 10.8 | 9.71 ± 9.14 | 7.39 ± 3.36 |
|  | PI127826 | 1 | — | — | 0.24 ± 0.24 | 282.4 ± 116.2 | 521.0 ± 323.6 | 0.28 ± 0.18 |
|  | PI127827 | 3 | 0.01 ± 0.01 | 0.03 ± 0.03 | — | — | — | 0.34 ± 0.21 |
|  | LA1353 | 3 | 0.20 ± 0.12 | 0.01 ± 0.01 | — | — | — | 2.56 ± 0.84 |
| S. habrochaites (f. glabratum) | PI126449 | 4 | — | — | 0.22 ± 0.22 | — | — | 8.34 ± 2.61 |
|  | PI134417 | 3 | — | — | — | — | — | 13.41 ± 5.98 |
|  | PI134418 | 4 | — | — | — | — | — | 3.08 ± 1.10 |
|  | PI251304 | 3 | — | — | — | 0.21 ± 0.21 | — | 7.23 ± 2.81 |
|  | IVT701631 | 4 | — | — | — | 3.35 ± 3.21 | — | 7.27 ± 6.31 |
|  | LA407 | 5 | — | — | — | 0.96 ± 0.96 | — | 3.64 ± 0.92 |
|  | GI1560 | 3 | — | — | — | 11.1 ± 6.6 | 3.76 ± 3.76 | 3.48 ± 0.57 |
|  | LA1840 | 5 | 0.02 ± 0.02 | 0.01 ± 0.01 | 0.05 ± 0.05 | 0.08 ± 0.05 | 0.88 ± 0.88 | 0.12 ± 0.05 |
| S. peruvianum | LA1708 | 5 | 0.09 ± 0.09 | 0.07 ± 0.03 | 1.13 ± 0.68 | 0.54 ± 0.54 | — | 2.88 ± 0.86 |
| S. lycopersicum | Motelle | 6 | 0.08 ± 0.06 | 0.02 ± 0.01 | — | — | — | 0.54 ± 0.17 |
|  | Mogeor | 6 | 0.08 ± 0.05 | 0.06 ± 0.05 | — | — | 0.38 ± 0.38 | 2.24 ± 0.91 |
|  | Monalbo | 6 | 0.42 ± 0.15 | 0.10 ± 0.05 | 0.60 ± 0.22 | — | 0.51 ± 0.34 | 1.37 ± 0.11 |
|  | Moneymaker | 7 | 0.07 ± 0.07 | 0.01 ± 0.01 | 0.07 ± 0.07 | 0.11 ± 0.11 | — | 3.35 ± 2.41 |
|  | Pitenza | 6 | 0.17 ± 0.10 | 0.07 ± 0.04 | 0.07 ± 0.07 | — | — | 1.11 ± 0.21 |

1 = highest repellence; 7 = least repellence. Semio-chemicals (μg 24 h$^{-1}$ 10 g$^{-1}$ FW) related to repellence emitted by wild tomato and cultivated tomato, in comparison to caryophyllene which is present in all accessions. Values indicate means (±SE) (n = 6).

Example 3

Bioassays with Selected Components and Mixtures of these Components 3.1 Material and Methods β-phellandrene, zingiberene and curcumene were not commercially available and had to be synthesised. Zingiberene and R-curcumene were isolated from ginger oil and 7-epi zingiberene and S-curcumene from S. habrochaites (PI27826) leaf material after Millar (1998, J. Nat. Prod 61, 1025).

Host preference with and without manipulated headspace by B. tabaci was explored in free choice assays. In each setup four cultivated tomatoes (cv. Moneymaker) were tested as described earlier. For the bioassays with volatiles rubber septa (Sigma Aldrich Z167258) were extracted with $CH_2Cl_2$ for 24 hours and dried to the air for 3 days. The desired blend of volatiles was added to the rubber septa in 100 μl hexane. Bioassays with pure components, or mixtures of pure components were carried out as described above.

3.2 Results

Figure 2A:
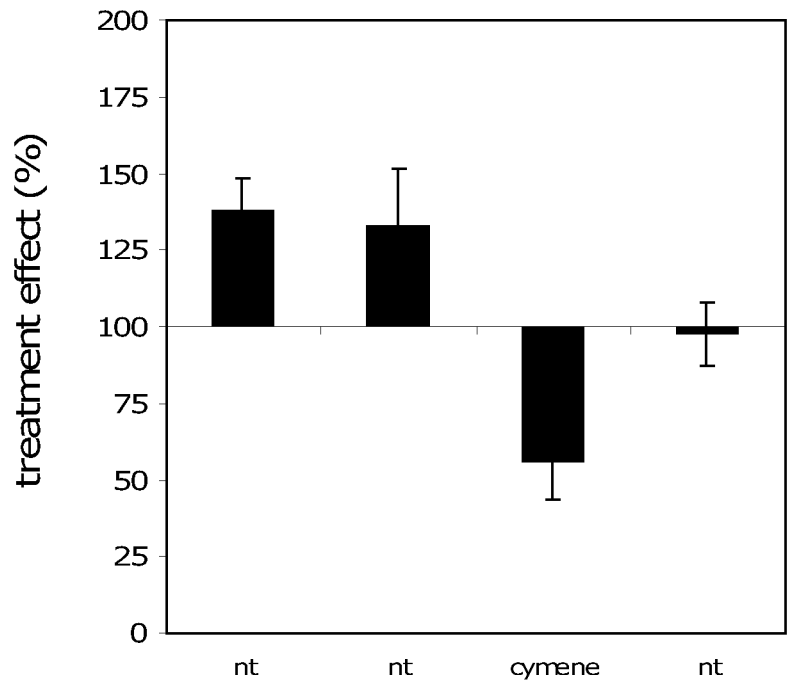
Figure 2B:
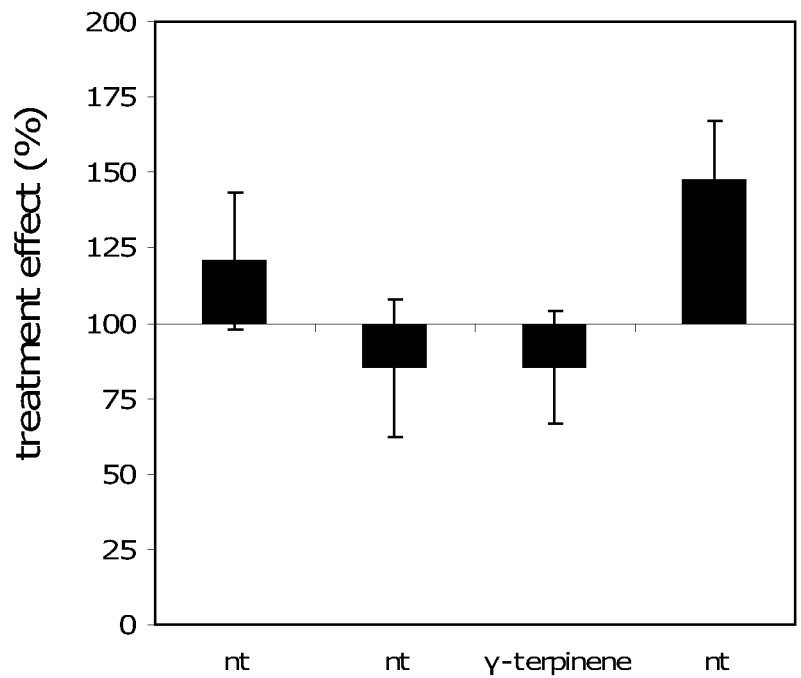
Figure 2C:
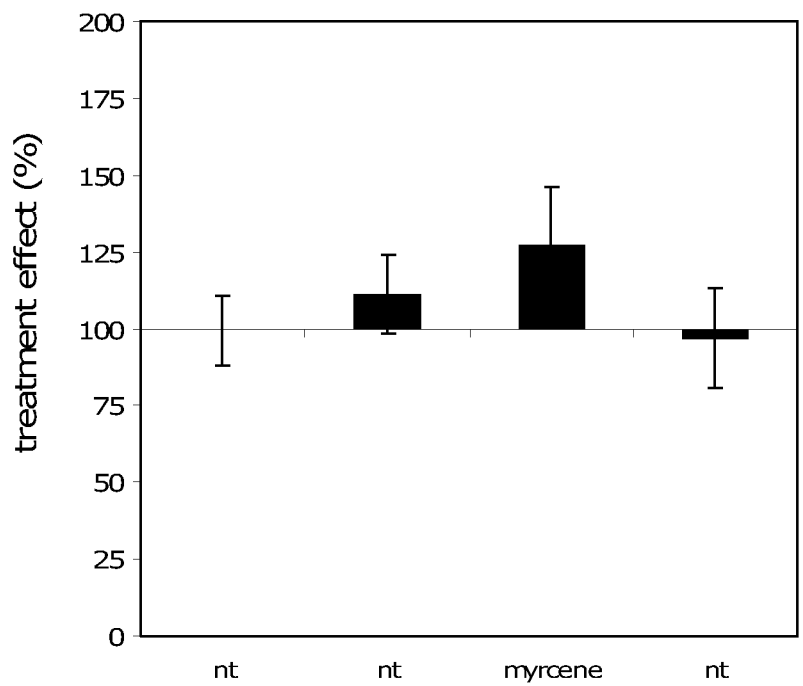
Figure 2D:
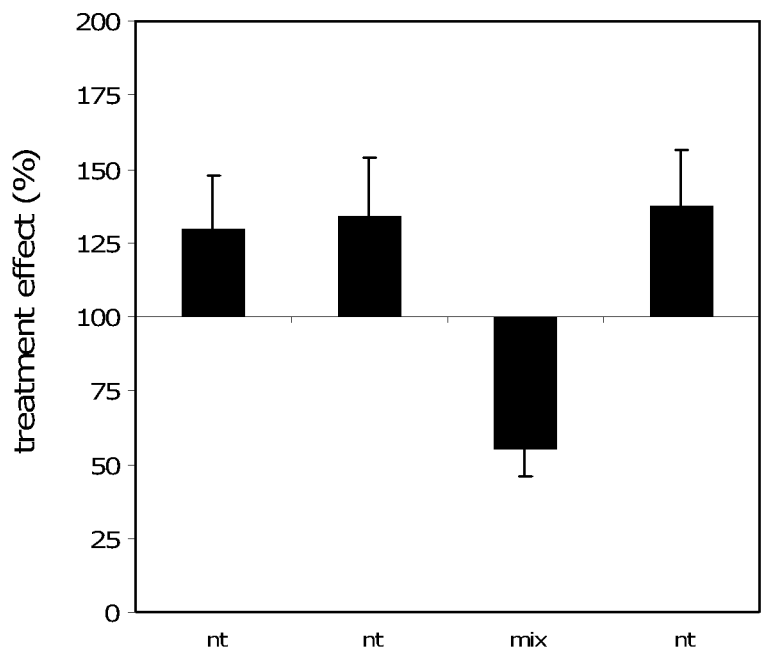
Figure 2E:
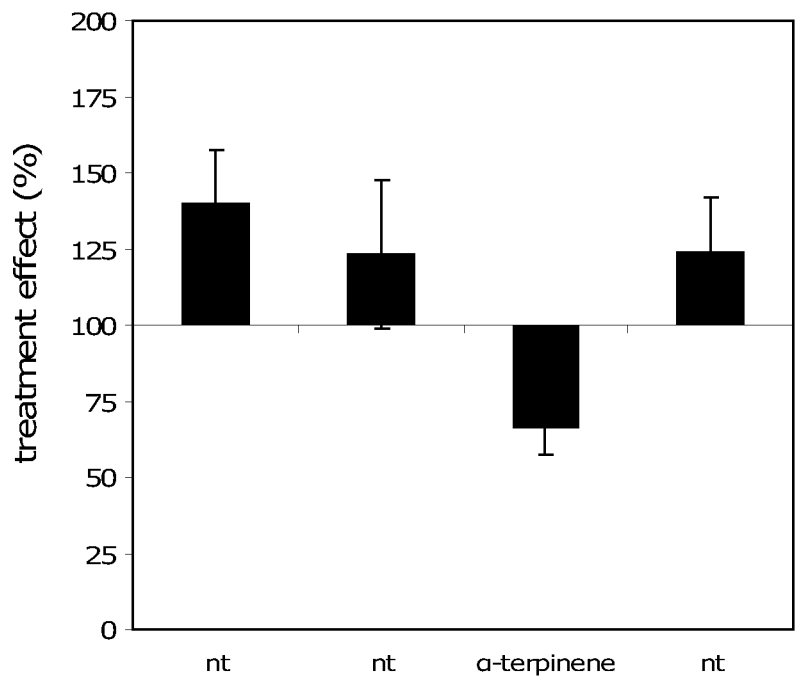
Figure 2F:
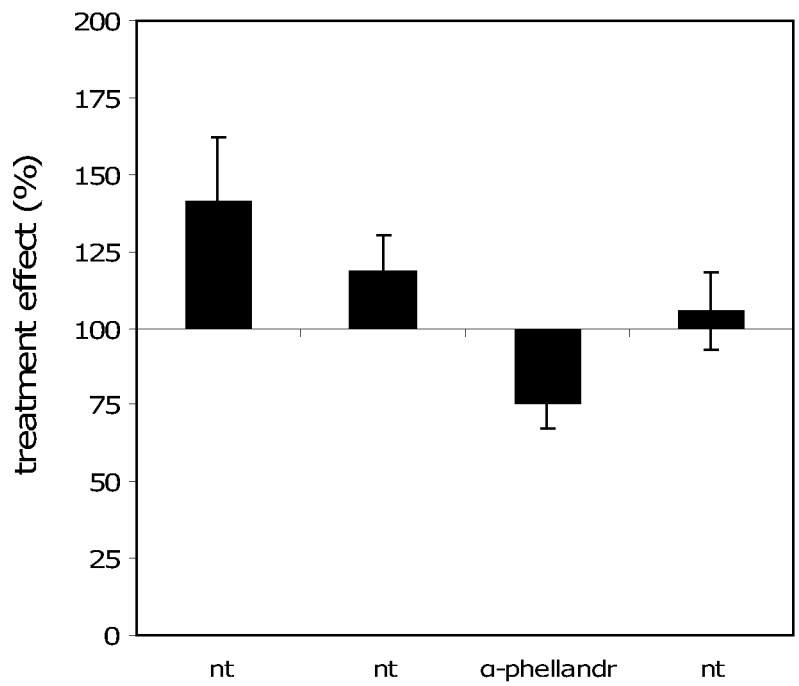
Figure 2G:
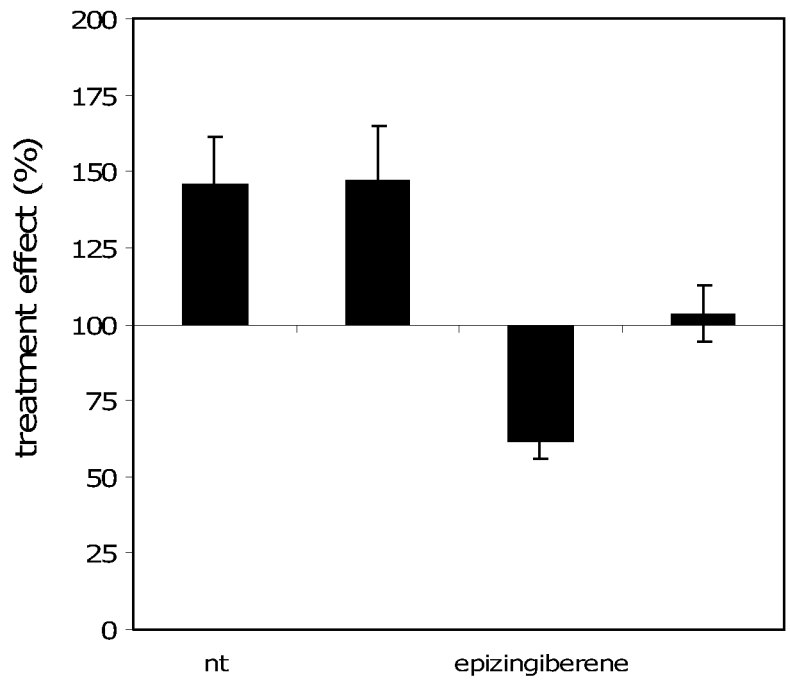
Figure 2H:
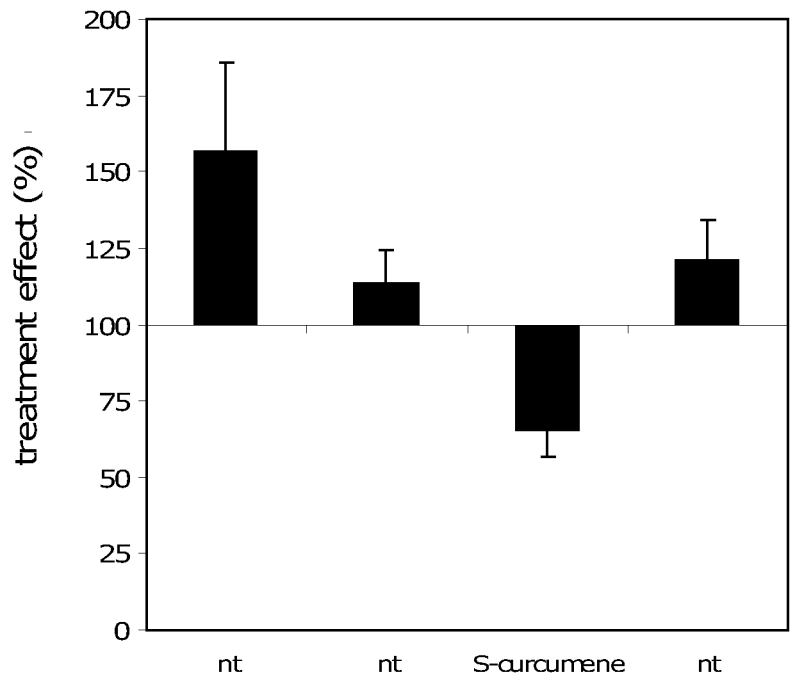
Figure 2I:
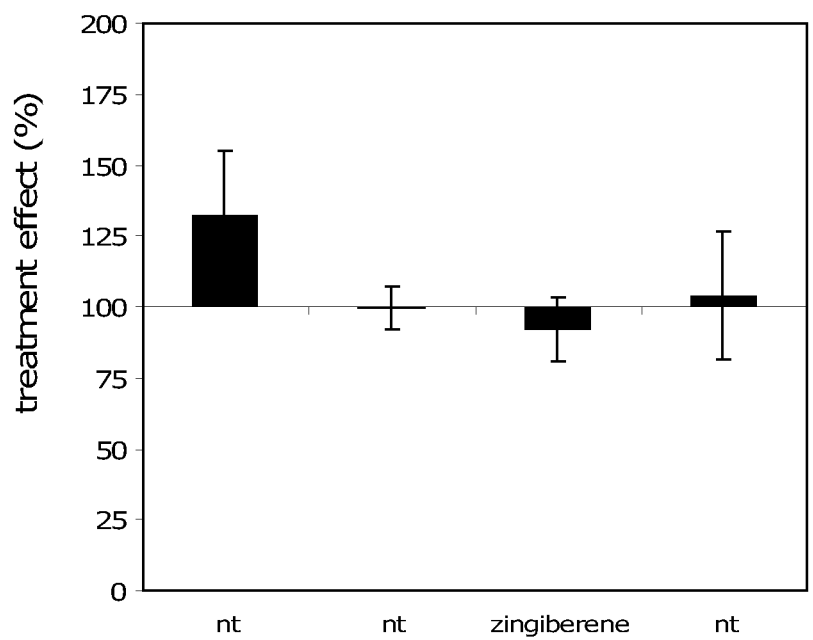
Figure 2J:
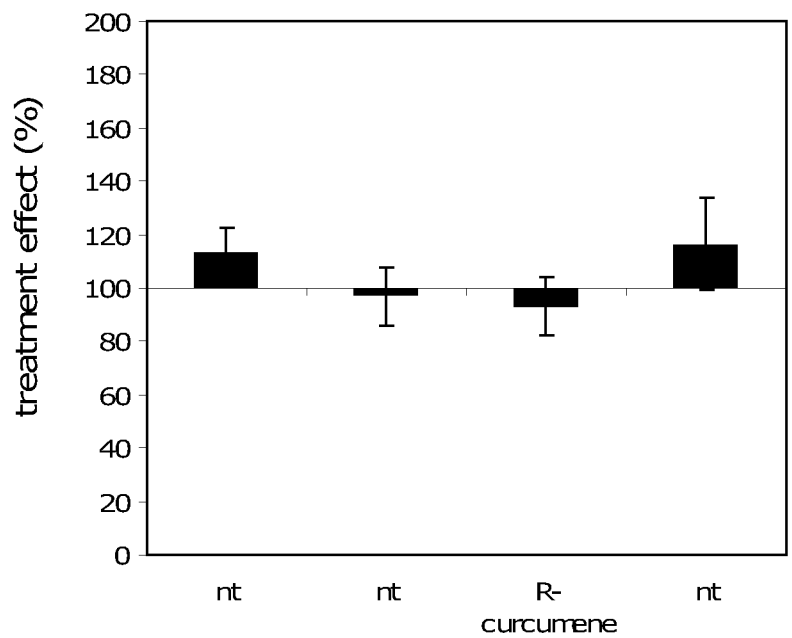

To positively confirm the correlation between the 7 candidate components and B. tabaci behaviour, host preference was assayed in bioassays with pure components. The desired (blend of) pure volatile chemicals were added, as described above, to the Moneymaker background on filter paper cards. In the absence of foreign volatiles the percentage recaptured B. tabaci on each of the four Moneymaker plants did not deviate significantly from the expected 25% (data not shown). However, when one of the plants was treated with 10 μg p-cymene, the level of attraction of this plant decreased significantly, compared to the same plant in the untreated setup. The percentage of whiteflies visiting the treated plant decreased with 44% on average (p<0.001) (FIG. 2A) while the untreated plants harboured increased numbers of B. tabaci. In general, when a synthetic component had a repellent effect on B. tabaci, the plants with empty carriers became increasingly more attractive (FIG. 2). Application of γ-terpinene to the Moneymaker background appeared to improve repellence, though no significant behavioural effect was established (p=0.102) (FIG. 2B). To assess whether the sum of these three components would yield a greater effect than p-cymene alone, a mixture of p-cymene: γ-terpinene: β-myrcene in the same ratio as found in accession LA2560 (1:12:3) was tested. This resulted in decreased plant visits with 45% on average (p<0.001) (FIG. 2D). Additional monoterpenes, derived from the Introgression-line analyses, α-phellandrene and α-terpinene both decreased tomato attractiveness significantly (p=0.030 and 0.014, respectively) (FIG. 2E,F). Finally, both sesquiterpenes tested, tomato-derived epizingiberene as well as its oxidation product S-curcumene, also had a clear repellent effect (p<0.001) (FIG. 2G,H).

Example 4

Linking Tomato Volatiles Directly to B. tabaci Response

Electroantennography (EAG) was employed to confirm the responsiveness of the atennae to $10^{-3}$ dilution in paraffin oil (Uvasol, Merck) of the chemicals described. Small pieces of filter paper (2 cm2; Schleicher & Schuell, Dassel, Germany) were soaked with 100 µl of the standard dilution or praffin oil only (control). The filter paper was inserted into a 10-ml glass syringe (Poulten & Graf GmbH, Wertheim, Germany). A reproducible stimulus was supplied by puffing 5 ml of air over the antenna (Schutz et al., 1999). The EAG response was recorded for each standard ($10^{-3}$) dilution. The response to paraffin oil was considered as a negative control and was subtracted from all the reported EAG measurements. The EAG response expressed as a potential difference across the electrodes (in mV) for the different pure chemicals is given in the right-hand column of Table 5.

Example 5

Bioassays in an Introgression Library

Because of the interesting repellence levels found in the *S. pennelli* accessions an introgression library (parents *S. pennelli* LA716×*S. lycopersicum* cv Moneyberg) was subsequently screened in bioassays (FIG. 3). Several lines with significantly decreased attraction compared to the susceptible parent, were selected. The headspace composition of these selected lines as well as the Moneyberg-parent were identified. Concentrations of α-phellandrene, α-terpinene and p-cymene were significantly higher in the selected lines compared to Moneyberg headspace.

The invention claimed is:

1. A method for repelling whiteflies, comprising: administering a repellant composition one or more times to a plurality of crop plants in an area susceptible to whitefly infestation, wherein the repellant composition comprises one or more repellant compounds selected from the group consisting of para-cymene, gamma-terpinene, alpha-terpinene, alpha-phellandrene and epizingiberene; and administering an attractant composition one or more times to one or more trap plants and/or trap materials, wherein the attractant composition comprises one or more attractant compounds selected from the group consisting of beta-phellandrene, limonene and 2-carene.

2. The method of claim 1, wherein said repellant composition is substantially free of other terpene or terpenoid compounds.

3. The method of claim 1, wherein said repellant composition is a liquid.

4. The method of claim 3, wherein said repellant composition is a volatile liquid.

5. The method of claim 1, wherein the repellant composition is not a naturally occurring head-space composition of plants, such as tomato plants.

6. The method of claim 1, wherein the attractant compound is chemically synthesized.

7. The method of claim 1, wherein said attractant composition is added by applying said composition to a support material and placing the support material onto, between, or near said crop plants and/or said trap plants or trap materials.

8. The method of claim 1, wherein the attractant composition consists of attractant compounds.

9. The method of claim 1, wherein the attractant composition consists of one attractant compound selected from the group consisting of beta-phellandrene, limonene and 2-carene.

10. The method of claim 1, wherein the attractant composition consists of two attractant compounds selected from the group consisting of beta-phellandrene, limonene and 2-carene.

11. The method of claim 1, wherein the attractant composition comprises no more than two attractant compounds selected from the group consisting of beta-phellandrene, limonene and 2-carene.

12. A method for repelling whiteflies, comprising: administering a repellant composition one or more times to a plurality of crop plants in an area susceptible to whitefly infestation, wherein the repellant composition consists of two repellant compounds selected from the group consisting of para-cymene, gamma-terpinene, alpha-terpinene, alpha-phellandrene and epizingiberene.

13. The method of claim 12, wherein said repellant composition is a liquid.

14. The method of claim 13, wherein said repellant composition is a volatile liquid.

15. The method of claim 12, wherein the repellant composition is not a naturally occurring head-space composition of plants, such as tomato plants.

16. The method of claim 12, wherein the repellant compound is chemically synthesized.

17. The method of claim 12, wherein said repellant composition is added by applying said repellant composition to a support material and placing the support material onto, between, or near said crop plants.

18. The method of claim 12, wherein said repellant composition is substantially free of other terpene or terpenoid compounds.

19. The method of claim 12, wherein the repellant composition comprises no more than two repellant compounds selected from the group consisting of para-cymene, gamma-terpinene, alpha-terpinene, alpha-phellandrene and epizingiberene.

20. The method according to claim 12, wherein the repellant composition comprises one or more repellant compounds selected from the group consisting of gamma-terpinene, alpha-terpinene, alpha-phellandrene and epizingiberene.

21. The method according to claim 12, wherein the repellant composition comprises epizingiberene.

22. The method according to claim 12, further comprising assessing whitefly infestation in the plurality of crop plants.

* * * * *